US010253321B2

(12) United States Patent
Minshull et al.

(10) Patent No.: US 10,253,321 B2
(45) Date of Patent: Apr. 9, 2019

(54) METHODS, COMPOSITIONS AND KITS FOR A ONE-STEP DNA CLONING SYSTEM

(71) Applicant: DNA 2.0, Inc., Menlo Park, CA (US)

(72) Inventors: Jeremy Minshull, Los Altos, CA (US); Jon Ness, Redwood City, CA (US)

(73) Assignee: DNA2.0, INC., Newark, CA (US)

( * ) Notice: Subject to any disclaimer, the term of this patent is extended or adjusted under 35 U.S.C. 154(b) by 433 days.

(21) Appl. No.: 14/881,004

(22) Filed: Oct. 12, 2015

(65) Prior Publication Data
US 2016/0032295 A1    Feb. 4, 2016

Related U.S. Application Data

(63) Continuation-in-part of application No. 13/875,277, filed on May 1, 2013, now Pat. No. 9,206,433.

(51) Int. Cl.
| | |
|---|---|
| C12Q 1/68 | (2018.01) |
| C07H 21/00 | (2006.01) |
| C12P 19/34 | (2006.01) |
| C12N 15/64 | (2006.01) |
| C12N 15/66 | (2006.01) |

(52) U.S. Cl.
CPC ............ *C12N 15/64* (2013.01); *C12N 15/66* (2013.01)

(58) Field of Classification Search
CPC .................................. C12P 19/34; C12Q 1/68
See application file for complete search history.

(56) References Cited

U.S. PATENT DOCUMENTS

| | | | |
|---|---|---|---|
| 5,888,732 A | 3/1999 | Hartley et al. | |
| 9,206,433 B2 * | 12/2015 | Minshull | C12N 15/66 |
| 2003/0118994 A1 | 6/2003 | Blackburn et al. | |
| 2005/0069929 A1 | 3/2005 | Chestnut et al. | |
| 2009/0298088 A1 | 12/2009 | Belyaev et al. | |
| 2009/0328244 A1 | 12/2009 | Chesnut et al. | |
| 2010/0291633 A1 | 11/2010 | Selmer et al. | |
| 2011/0244521 A1 | 10/2011 | Nagai et al. | |
| 2011/0263024 A1 | 10/2011 | Marillonnet et al. | |
| 2012/0259607 A1 | 10/2012 | Hillson | |
| 2012/0301873 A1 | 11/2012 | Sassano et al. | |
| 2013/0267021 A1 | 10/2013 | Weber et al. | |

FOREIGN PATENT DOCUMENTS

| | | |
|---|---|---|
| WO | WO 11/154147 A1 | 12/2011 |
| WO | WO 14/179499 A1 | 11/2014 |

OTHER PUBLICATIONS

Beck et al. mAbs 3(5) : 415-416 (Year: 2011).*
Kotera et al., J. of Biotechnology 137 :1-7 (Year: 2008).*
Lu. Trends in Biotechnology 23(4) :1999-207 (Year: 2005).*
Martinez-Salas. Current Opinion in Biotechnology (Year: 1999).*
Van Pijkeren et al.Nucleic Acids Research 40(10) : e76 (Year: 2012).*
Xin et al. Microbial cell factories 16 : 116 (Year: 2017).*
"Gene Characterization Kits," Stratagene Catalog, p.39, (1988) ]. [Author Unknown].
"GeneAmpTM DNA Amplification Reagent Kit," Perkin Elmer Cetus, Product Insert, 2 pages, (1988). [Author Unknown].
Engler et al., "A One Pot, One Step, Precision Cloning Method with High Throughput Capability," PLoS ONE, 3(11):e3647, pp. 1-7, (2008).
Engler et al., "Golden Gate Shuffling: A One-Pot DNA Shuffling Method Based on Type IIs Restriction Enzymes," PLoS ONE, 4(5):e5553, pp. 1-9, (2009).
Padgett et al., "Creating seamless junctions independent of restriction sites in PCR cloning," Gene, 168:31-35, (1996).
Reyrat et al., "Counterselectable Markers: Untapped Tools for Bacterial Genetics and Pathogenesis," Infection and Immunity, 66(9):4011-4017, (1998).
Szybalski et al., "Class-IIS restriction enzymes—a review," Gene, 100:13-26, (1991).
U.S. Appl. No. 13/875,277, Final Office Action dated May 18, 2015.
U.S. Appl. No. 13/875,277, Non-Final Office Action dated Dec. 22, 2014.
U.S. Appl. No. 13/875,277, Notice of Allowance dated Aug. 4, 2015.
Weber et al., "A Modular Cloning System for Standardized Assembly of Multigene Constructs," PLoS ONE, 6(2):e16765, pp. 1-11, (2011).
WIPO Application No. PCT/US2014/036251, PCT International Preliminary Report on Patentability dated Nov. 3, 2015.
WIPO Application No. PCT/US2014/036251, PCT International Search Report dated Sep. 19, 2014.
WIPO Application No. PCT/US2014/036251, PCT Written Opinion of the International Searching Authority dated Sep. 19, 2014.

\* cited by examiner

*Primary Examiner* — Ethan C Whisenant
(74) *Attorney, Agent, or Firm* — Alston & Bird LLP

(57) ABSTRACT

Methods and kits for joining three or more polynucleotides to form a product polynucleotide are provided. Such a method includes forming a reaction mixture comprising (i) a vector fragment whose ends have four base overhangs resulting from cleavage of a vector with a first type IIs enzyme, (ii) a first insert nucleic acid with a four base overhang at one end resulting from cleavage by the first type IIs enzyme and a three base overhang at the other end resulting from cleavage by the second type IIs enzyme; and (iii) a second insert nucleic acid with a four base overhang at one end resulting from cleavage by the first type IIs enzyme and a three base overhang at the other end resulting from cleavage by the second type IIs enzyme, and (iv) a ligase. The four base overhangs of the vector ligate with the four base overhangs of the first and second inserts and the three base overhangs of the first and second inserts ligate with each other or three base overhangs of a spacer nucleic acid resulting from cleavage with the second type IIs enzyme to form a product polynucleotide in which the first and second insert nucleic acids are joined to the vector fragment.

20 Claims, 2 Drawing Sheets

Figure 1:
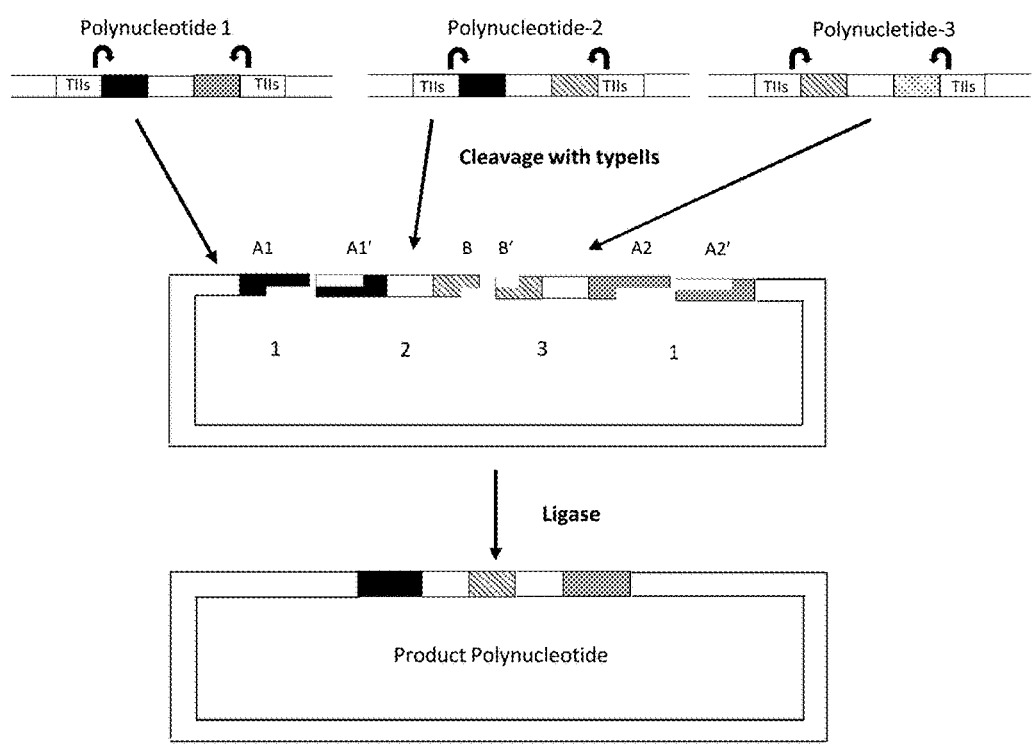

Specification includes a Sequence Listing.

METHODS, COMPOSITIONS AND KITS FOR A ONE-STEP DNA CLONING SYSTEM

1. CROSS REFERENCE TO RELATED APPLICATIONS

The present application is a continuation-in-part of Ser. No. 13/875,277 filed May 1, 2013, which is incorporated by reference in its entirety for all purposes.

2. INCORPORATION BY REFERENCE OF SEQUENCE LISTING

Sequences from the application are contained in a txt sequence listing designated 468927_SEQLST.txt of 7,177 bytes, created Oct. 9, 2015, which is incorporated by reference.

3. FIELD OF THE INVENTION

Methods, compositions and kits useful for a one-step molecular cloning system are provided. In certain embodiments the methods comprise combining into a mixture: two or more polynucleotides each comprising two sequences recognized by typeIIs restriction enzymes; typeIIs restriction enzymes and a DNA ligase so that the polynucleotides are joined in a directed manner. Methods for designing and synthesizing vectors useful for practicing of the method are also disclosed. Methods for creating combinatorial libraries using the method are also disclosed.

4. BACKGROUND OF THE INVENTION

The cloning of DNA segments is performed as a daily routine in many research labs. It is frequently performed in order to move a first polynucleotide sequence from a first vector into a second vector, where the second vector performs a function that is not performed by the first. Differences between the two vectors may include differences in selectable markers or differences in replicative sequences. They may also include differences in vector sequence elements that may directly interact with the first polynucleotide, for example by affecting expression of a gene encoded by the first polynucleotide, or by encoding polypeptides that interact with or are joined to polypeptides encoded by the first polynucleotide.

The specialized vectors used for subcloning DNA segments are functionally diverse. These include but are not limited to: vectors for expressing genes in various organisms; for regulating gene expression; for providing tags to modify polypeptide properties such as solubility, localization, affinity for a substrate, color, fluorescence, characteristics that facilitate protein purification and characteristics that facilitate tracking of proteins in cells; for modifying the cloned DNA segment (e.g., generating deletions); for the synthesis of probes (e.g., riboprobes); for the preparation of templates for DNA sequencing; for the identification of protein coding regions; for the fusion of various protein-coding regions; for expressing one or more enzymes to catalyze a reaction and for providing large amounts of the DNA of interest. It is common that a particular investigation will involve subcloning the DNA segment of interest into several different specialized vectors.

Simple subclonings, for example those where a single DNA segment to be subcloned is not large and the restriction sites are compatible with those of the subcloning vector, can be done in one day. However, it is frequently desirable to combine more than two polynucleotides, and the efficiency of such cloning reactions is significantly lower, resulting in more time, effort and money spent on creating the final desired DNA molecule. There is thus a need for a rapid and reliable method for moving multiple polynucleotides into one or more specialized vectors.

5. SUMMARY OF THE INVENTION

The present invention relates to nucleic acids, vectors and methods for combining three or more polynucleotides in a single reaction.

A method for assembly of three or more polynucleotides in a single reaction is described. The method takes advantage of DNA digestion by one or more restriction enzymes that recognize a non-palindromic sequence, and that cleave outside their recognition sequences, for example typeIIs restriction enzymes. Different typeIIs restriction enzymes may produce different length single-stranded overhangs following cleavage of DNA by a typeIIs restriction enzyme, one of the ends produced by such cleavage lacks any part of the recognition sequence.

A method of forming a product polynucleotide comprising: forming a reaction mixture comprising (i) a vector fragment whose ends have four base overhangs resulting from cleavage of a vector with a first typeIIs restriction enzyme, (ii) a first insert nucleic acid with a four base overhang resulting from cleavage with a first typeIIs restriction enzyme and a three base overhang at the other end resulting from cleavage with a second typeIIs restriction enzyme, (iii) a second insert nucleic acid with four base overhang at one end resulting from cleavage with a first typeIIs restriction enzyme and a three base overhang at the other end resulting from cleavage with a second typeIIs restriction enzyme; and (iv) a ligase, wherein the four base overhangs of the vector ligate with the four base overhangs of the first and second inserts and the three base overhangs of the first and second inserts ligate with each other to form a product polynucleotide in which a first and second insert nucleic acids is joined to the vector fragment. The method may further comprise a spacer nucleic acid with three base overhangs at each end resulting from cleavage with a second typeIIs restriction enzyme such that the three base overhangs of the first and second inserts ligate with the three base inserts of the spacer nucleic acid to form a product polynucleotide in which the spacer nucleic acid flanked by a first and second insert nucleic acids is joined to the vector fragment.

The product polynucleotide may encode a fusion protein comprising the polypeptides encoded by the first and second insert nucleic acids. The method of forming a product nucleotide, wherein joining of the three base overhang of the first insert nucleic acid and the three base overhang of the spacer generates a stop codon for the polypeptide encoded by the first insert nucleic acid. The method of forming a product nucleotide, wherein joining of the three base overhang of the second insert nucleic acid and the three base overhang of the spacer generates an initiation codon for other polypeptide encoded by the second insert nucleic acid. The method of forming a product nucleotide, wherein joining of the three base overhang of the first insert nucleic acid and the three base overhang of the spacer forms a glycine or alanine codon between the first and second polypeptides in a fusion protein. The method of forming a product nucleotide, wherein joining of the three base overhang of the first insert nucleic acid and the three base overhang of the second insert nucleic acid forms a glycine or alanine codon between the first and second polypeptides in a fusion protein.

The first typeIIs restriction enzyme is BsaI and the second typeIIs restriction enzyme is selected from BspQI or SapI. The first and second insert polynucleotides may collectively encode a polypeptide. The first and second insert polynucleotides preferably encode antibody heavy and light chains. The spacer nucleic acid may comprise a promoter placed in operable linkage with the second insert polynucleotide in the product polynucleotide. The spacer nucleic acid may comprise an internal ribosome entry site (IRES) or a cis-acting hydrolysable element (CHYSEL/2A) placed in operable linkage with the second insert polynucleotide in the product polynucleotide. The vector fragment comprises a promoter placed in operable linkage with the first insert polynucleotide in the product polynucleotide. The vector may further comprise a counter-selectable marker. The counter-selectable marker is selected from a group consisting of sacB, rpsL, tetAR, pheS, thyA, lacY, gata-1, ccdB, kid and barnase. Each of the polypeptides forming the product polynucleotide, the vector fragment, the first and second insert polynucleotides and the spacer polynucleotide lack recognition sites for the typeIIs restriction enzymes that generated its overhang ends. The overhangs are generated by the first and second typeIIs restriction enzymes and joining of the polynucleotide overhangs is in the same reaction mixture. The overhangs may be generated before forming the reaction mixture.

The method of forming a product polynucleotide further comprises transforming the mixture into a host cell and growing the host cell under conditions that select for the presence of a selectable marker and, optionally, isolating the product polynucleotide from the host cell.

Also included is a kit for forming a product polynucleotide comprising (i) a vector fragment whose ends have four base overhangs resulting from cleavage of a vector with a first typeIIs restriction enzyme, (ii) a spacer nucleic acid with three base overhangs at each end resulting from cleavage with a second typeIIs restriction enzyme, wherein the vector fragment and spacer nucleic acid can be combined with (iii) a first insert nucleic acid with a four base overhang at one end resulting from cleavage with a first typeIIs restriction enzyme and a three base overhang at the other end resulting from cleavage with a second typeIIs restriction enzyme, (iv) a second insert nucleic acid with a four base overhang at one end resulting from cleavage with a first typeIIs restriction enzyme and a three base overhang at the other end resulting from cleavage with a second typeIIs restriction enzyme, and (v) a ligase, wherein the four base overhangs of the vector ligate with the four base overhangs of the first and second inserts and the three base overhangs of the first and second inserts ligate with the three base overhangs of the spacer nucleic acid to form a product polynucleotide in which the spacer nucleic acid flanked by a first and second insert nucleic acids is joined to the vector fragment.

A kit comprising: a) an enzyme mixture comprising: i) a first typeIIs restriction endonuclease that recognizes a first typeIIs recognition sequence of six bases to generate four-base overhangs; ii) a second typeIIs restriction endonuclease that recognizes a second typeIIs recognition sequence of seven bases to generate three-base overhangs; iii) a DNA ligase; b) a reaction buffer, and c) instructions for incubating the enzyme mixture, the reaction buffer and the polynucleotides for a predetermined length of time, and transforming the mixture into a host cell. The kit further comprises a polynucleotide comprising a selectable marker and first and second typeIIs recognition sequences or a vector fragment and an insert polynucleotide comprising expression control elements or coupling elements, a counter-selectable marker and first and second typeIIs recognition sequences.

Other embodiments will be evident to those of ordinary skill in the art from the teachings contained herein in combination with what is known to the art.

6. BRIEF DESCRIPTION OF THE DRAWINGS

FIG. 1: is a schematic showing assembly of three polynucleotides in the presence of different typeIIs restriction endonucleases and a DNA ligase in a single reaction. Each polynucleotide comprises flanking typeIIs recognition sites such that cleavage with the typeIIs restriction endonucleases produces different length overhangs, two polynucleotides with different length overhangs at each end and one polynucleotide with the same length overhangs at each end. For example, cleavage with the first typeIIs restriction enzyme produces 4 base single-stranded DNA overhangs A1 and A2 such that the ends A1 and A1' are compatible ends and ends A2 and A2' are compatible ends; cleavage with the second typeIIs restriction enzyme produces 3 base single-stranded DNA overhangs B and B' that are compatible ends. Joining of compatible ends (A1 with A1', A2 with A2' and B with B') in the presence of DNA ligase produces the product polynucleotide. The typeIIs restriction endonuclease that produces 4 base overhangs is BsaI and the typeIIs that produces 3 base overhangs is selected from BspQ1 or SapI. For example 3 base overhangs when joining two polynucleotides that encode open reading frames (ORFs) may be selected from glycine (5'-GGN-3') or alanine (5'-GCN-3'), 4 base overhangs are selected from 5'-AAAA-3' or 5'-TTTT-3' or 5'-GGGG-3' or 5'-CCCC-3'. The first polynucleotide may include a selectable marker, an origin of replication and elements that confer regulation of gene expression which serves as a vector. The second and third polynucleotides collectively encode a single polypeptide.

Figure 2:
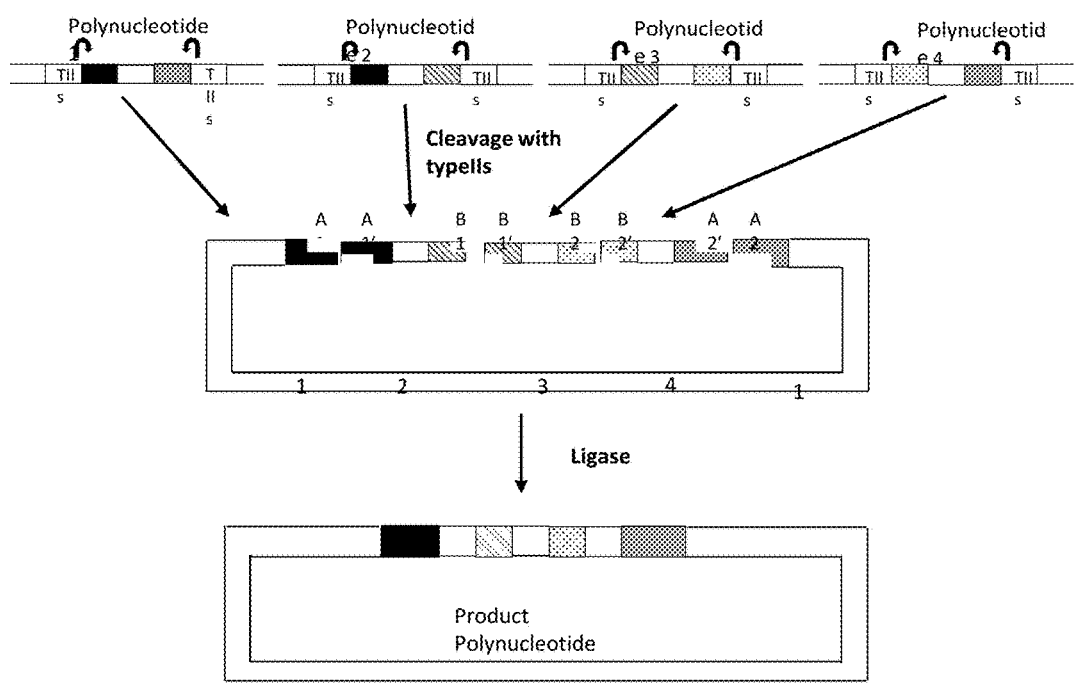

FIG. 2: is a schematic showing assembly of four polynucleotides in the presence of two typeIIs restriction endonucleases and a DNA ligase in a single reaction. Each polynucleotide comprises flanking typeIIs recognition sites such that cleavage with the typeIIs restriction endonucleases produces different length overhangs, two polynucleotides with different length overhangs at each end and two polynucleotides with the same length overhangs at each end. For example cleavage of polynucleotide 1 produces ends, each a 4 base overhang A1 and A2; cleavage of polynucleotide 2 produces ends, one a 4 base overhang A1' and one a 3 base overhang B1; cleavage of polynucleotide 3 produces ends, each a 3 base overhang B1' and B2; cleavage of polynucleotide 4 produces ends, one a 3 base overhang B2' and the other a 4 base overhang A2' such that overhangs A1 and A1' are compatible ends, A2 and A2' are compatible ends, B1 and BF are compatible ends and B2 and B2' are compatible ends. Joining of compatible ends in the presence of DNA ligase produces the product polynucleotide. The first polynucleotide may include a selectable marker, an origin of replication and elements that confer regulation of gene expression which serves as a vector. The second and fourth polynucleotides collectively encode a single polypeptide. The third polynucleotide that joins second and fourth polynucleotides may comprise expression control elements including transcriptional promoter(s) including bidirectional and dual promoters and/or an enhancer and/or a terminator, an element that modulates the efficiency of initiation of translation such as a ribosome binding site or a Kozak consensus sequence or an internal ribosome entry site (IRES) or a cis acting hydrolysable element (CHYSEL/2A) element such that the third or spacer polynucleotide flanked by the second and fourth polynucleotides is joined with the first polynucleotide or vector fragment.

7. DETAILED DESCRIPTION OF THE INVENTION

7.1 Definitions

Use of the singular forms "a," "an," and "the" include plural references unless the context clearly dictates otherwise. Thus, for example, reference to "a polynucleotide" includes a plurality of polynucleotides, reference to "a substrate" includes a plurality of such substrates, reference to "a variant" includes a plurality of variants, and the like.

Terms such as "connected," "attached," "linked," and "conjugated" are used interchangeably herein and encompass direct as well as indirect connection, attachment, linkage or conjugation unless the context clearly dictates otherwise. Where a range of values is recited, it is to be understood that each intervening integer value, and each fraction thereof, between the recited upper and lower limits of that range is also specifically disclosed, along with each subrange between such values. The upper and lower limits of any range can independently be included in or excluded from the range, and each range where either, neither or both limits are included is also encompassed within the invention. Where a value being discussed has inherent limits, for example where a component can be present at a concentration of from 0 to 100%, or where the pH of an aqueous solution can range from 1 to 14, those inherent limits are specifically disclosed. Where a value is explicitly recited, it is to be understood that values which are about the same quantity or amount as the recited value are also within the scope of the invention. Where a combination is disclosed, each sub combination of the elements of that combination is also specifically disclosed and is within the scope of the invention. Conversely, where different elements or groups of elements are individually disclosed, combinations thereof are also disclosed. Where any element of an invention is disclosed as having a plurality of alternatives, examples of that invention in which each alternative is excluded singly or in any combination with the other alternatives are also hereby disclosed; more than one element of an invention can have such exclusions, and all combinations of elements having such exclusions are hereby disclosed.

Unless defined otherwise herein, all technical and scientific terms used herein have the same meaning as commonly understood by one of ordinary skill in the art to which this invention belongs. Singleton, et al., *Dictionary of Microbiology and Molecular Biology*, 2nd Ed., John Wiley and Sons, New York (1994), and Hale & Marham, *The Harper Collins Dictionary of Biology*, Harper Perennial, N Y, 1991, provide one of skill with a general dictionary of many of the terms used in this invention. Although any methods and materials similar or equivalent to those described herein can be used in the practice or testing of the present invention, the preferred methods and materials are described. Unless otherwise indicated, nucleic acids are written left to right in 5' to 3' orientation; amino acid sequences are written left to right in amino to carboxy orientation, respectively. The terms defined immediately below are more fully defined by reference to the specification as a whole.

Standard A-T and G-C base pairs form under conditions which allow the formation of hydrogen bonds between the N3-H and C4-oxy of thymidine and the NI and C6-NH2, respectively, of adenosine and between the C2-oxy, N3 and C4-NH2, of cytidine and the C2-NH2, N'—H and C6-oxy, respectively, of guanosine. Thus, for example, guanosine (2-amino-6-oxy-9-.beta.-D-ribofuranosyl-purine) may be modified to form isoguanosine (2-oxy-6-amino-9-.beta.-D-ribofuranosyl-purine). Such modification results in a nucleoside base which will no longer effectively form a standard base pair with cytosine. However, modification of cytosine (1-.beta.-D-ribofuranosyl-2-oxy-4-amino-pyrimidine) to form isocytosine (1-.beta.-D-ribofuranosyl-2-amino-4-oxy-pyrimidine-) results in a modified nucleotide which will not effectively base pair with guanosine but will form a base pair with isoguanosine (U.S. Pat. No. 5,681,702 to Collins et al., hereby incorporated by reference in its entirety). Isocytosine is available from Sigma Chemical Co. (St. Louis, Mo.); isocytidine may be prepared by the method described by Switzer et al. (1993) Biochemistry 32:10489-10496 and references cited therein; 2'-deoxy-5-methyl-isocytidine may be prepared by the method of Tor et al., 1993, J. Am. Chem. Soc. 115:4461-4467 and references cited therein; and isoguanine nucleotides may be prepared using the method described by Switzer et al., 1993, supra, and Mantsch et al., 1993, Biochem. 14:5593-5601, or by the method described in U.S. Pat. No. 5,780,610 to Collins et al., each of which is hereby incorporated by reference in its entirety. Other non-natural base pairs may be synthesized by the method described in Piccirilli et al., 1990, Nature 343:33-37, hereby incorporated by reference in its entirety, for the synthesis of 2,6-diaminopyrimidine and its complement (1-methylpyrazolo-[4,3]pyrimidine-5,7-(4H,6H)-dione. Other such modified nucleotidic units which form unique base pairs are known, such as those described in Leach et al. (1992) J. Am. Chem. Soc. 114:3675-3683 and Switzer et al., supra.

The term "coupling element" refers to a DNA sequence that allows the expression of a first polypeptide to be linked to the expression of a second polypeptide. Internal ribosome binding sites and cis-acting hydrolase elements are examples of coupling elements.

The term "compatible ends" refers to two ends of polynucleotide molecules that are both blunt or that both possess overhangs of the same length and directionality (i.e. either are 5'-overhangs or both are 3'-overhangs) and with perfectly complementary sequences, such that said DNA ends form standard Watson-Crick base pairs (i.e. C with G and T or U with A). Ends are "compatible" with each other when these criteria are met. When at least one end of a compatible pair is phosphorylated, the ends can be joined by a DNA ligase and are "ligatable ends".

Complementarity or Complementary sequences is a property shared between two nucleic acid sequences, such that when they are aligned antiparallel to each other, the nucleotide bases at each position will be complementary. Two bases are complementary if they form Watson-Crick base pairs (i.e. C with G and T or U with A).

The term "Contiguous Polypeptide" refers to an amino acid sequence that is encoded in the same open reading frame of a single physical polynucleotide sequence without any stop codons.

The phrase "DNA sequence" refers to a contiguous nucleic acid sequence. The sequence can be either single stranded or double stranded, DNA or RNA, but double stranded DNA sequences are preferable. The sequence can be an oligonucleotide of 6 to 20 nucleotides in length to a full length genomic sequence of thousands or hundreds of thousands of base pairs.

The term "expression system" refers to any in vivo or in vitro biological system that is used to produce one or more polypeptide encoded by a polynucleotide.

The term "annealing temperature" or "melting temperature" or "transition temperature" refers to the temperature at which a pair of nucleic acids is in a state intermediate between being fully annealed and fully melted. The term refers to the behavior of a population of nucleic acids: the "annealing temperature" or "melting temperature" or "transition temperature" is the temperature at which 50% of the molecules are annealed and 50% are separate. Annealing temperatures can be determined experimentally. There are also methods well known in the art for calculating these temperatures. Examples of temperature used during the incubation steps described herein are 4° C., or 5° C., or 6° C., or 7° C., or 8° C., or 9° C., or 10° C., or 11° C., or 12° C., or 13° C., or 14° C., or 15° C., or 16° C., or 17° C., or 18° C., or 19° C., or 20° C., or 21° C., or 22° C., or 23° C., or 24° C., or 25° C., or 26° C., or 27° C., or 28° C., or 29° C., or 30° C., or 31° C., or 32° C., or 33° C., or 34° C., or 35° C., or 36° C., or 37° C., or 38° C., or 39° C., or 40° C., or 41° C., or 42° C., or 43° C., or 44° C., or 45° C.

The term "Host" refers to any prokaryotic or eukaryotic organism that can be a recipient of a nucleic acid. A "host", as the term is used herein, includes prokaryotic or eukaryotic organisms that can be genetically engineered. For examples of such hosts, see Maniatis et al., Molecular Cloning. A Laboratory Manual, Cold Spring Harbor Laboratory, Cold Spring Harbor, N.Y. (1982). As used herein, the terms "host," "host cell," "host system" and "expression host" are used interchangeably.

The terms "nucleoside" and "nucleotide" refers to moieties which contain not only the known purine and pyrimidine bases, but also other heterocyclic bases which have been modified. Such modifications include methylated purines or pyrimidines, acylated purines or pyrimidines, or other heterocycles. Modified nucleosides or nucleotides can also include modifications on the sugar moiety, e.g., where one or more of the hydroxyl groups are replaced with halogen, aliphatic groups, or is functionalized as ethers, amines, or the like. The term "nucleotidic unit" is intended to encompass nucleosides and nucleotides.

The term "Overhang" or "DNA Overhang" refers to the single-stranded portion at the end of a double-stranded DNA molecule. Complementary overhangs are those which will base-pair with each other.

The term "One unit" as applied to restriction endonucleases refers to the amount of enzyme required to digest 1 μg of λ DNA in 1 hour at 37° C. in a total reaction volume of 50 μl.

The term "One unit" as applied to a DNA ligase refers to the amount of enzyme required to give 50% ligation of the 12-base pair cohesive ends of 1 μg of BstEII-digested □ DNA in a total reaction volume of 50 μl in 15 minutes at 45° C.

The phrase "predetermined time period" or "predetermined length of time" refers to a specified amount of time and the terms can be used interchangeably. A "predetermined period of time" can be on the order of seconds, minutes, hours, days, weeks, or months. For example, a "predetermined time period" can be between 1 and 59 minutes, or any increment between 1 and 2 hours, or any increment between 2 and 4 hours, or any increment between 4 and 6 hours, or any increment between 6 and 12 hours, or any increment between 12 and 24 hours, or any increment between 1 day and 2 days.

The terms "pseudo-ligatable ends" or "pseudo-compatible ends" refer to two ends of polynucleotide molecules that possess overhangs of the same length and directionality (i.e. both are 5'-overhangs, or both are 3'-overhangs) and with imperfectly paired complementary sequences, such that annealing of said DNA ends requires at least one non-standard Watson-Crick base pair (i.e. T or U with G), but which can nevertheless can be joined by a DNA ligase, albeit at a lower efficiency than ends that form only standard Watson-Crick base pairs.

The terms "polynucleotide," "oligonucleotide," "nucleic acid" and "nucleic acid molecule" and "gene" are used interchangeably herein to refer to a polymeric form of nucleotides of any length, and may comprise ribonucleotides, deoxyribonucleotides, analogs thereof, or mixtures thereof. This term refers only to the primary structure of the molecule. Thus, the term includes triple-, double- and single-stranded deoxyribonucleic acid ("DNA"), as well as triple-, double- and single-stranded ribonucleic acid ("RNA"). It also includes modified, for example by alkylation, and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), including tRNA, rRNA, hRNA, siRNA and mRNA, whether spliced or unspliced, any other type of polynucleotide which is an N- or C-glycoside of a purine or pyrimidine base, and other polymers containing nonnucleotidic backbones, for example, polyamide (e.g., peptide nucleic acids ("PNAs")) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA. There is no intended distinction in length between the terms "polynucleotide," "oligonucleotide," "nucleic acid" and "nucleic acid molecule," and these terms are used interchangeably herein. These terms refer only to the primary structure of the molecule. Thus, these terms include, for example, 3'-deoxy-2', 5'-DNA, oligodeoxyribonucleotide N3' P5' phosphoramidates, 2'-O-alkyl-substituted RNA, double- and single-stranded DNA, as well as double- and single-stranded RNA, and hybrids thereof including for example hybrids between DNA and RNA or between PNAs and DNA or RNA, and also include known types of modifications, for example, labels, alkylation, "caps," substitution of one or more of the nucleotides with an analog, internucleotide modifications such as, for example, those with uncharged linkages (e.g., methyl phosphonates, phosphotriesters, phosphoramidates, carbamates), with negatively charged linkages (e.g., phosphorothioates, phosphorodithioates), and with positively charged linkages (e.g., aminoalkylphosphoramidates, aminoalkylphosphotriesters), those containing pendant moieties, such as, for example, proteins (including enzymes (e.g. nucleases), toxins, antibodies, signal peptides, poly-L-lysine), those with intercalators (e.g., acridine, psoralen), those containing chelates (of, e.g., metals, radioactive metals, boron, oxidative metals), those containing alkylators, those with modified linkages (e.g., alpha anomeric nucleic acids), as well as unmodified forms of the polynucleotide or oligonucleotide. Where the polynucleotides are to be used to express encoded proteins, nucleotides that can perform that function or which can be modified (e.g., reverse transcribed) to perform that function are used. Where the polynucleotides are to be used in a scheme that requires that a complementary strand be formed to a given polynucleotide, nucleotides are used which permit such formation.

The term "polynucleotide vector" refers to a polynucleotide comprising a selectable marker.

The term "product polynucleotide" refers to the product of two or more polynucleotides cleaved by typeIIs restriction enzymes and joined by a DNA ligase after incubation in a mixture comprising the polynucleotides, the typeIIs restriction enzyme(s) and the DNA ligase.

The term "Recognition sequence" refers to a particular DNA sequence(s) which are recognized (and bound by) a protein, DNA, or RNA molecule, including a restriction endonuclease, a modification methylase, and a recombinase. For example, the recognition sequence for Cre recombinase is loxP which is a 34 base pair sequence comprised of two 13 base pair inverted repeats (serving as the recombinase binding sites) flanking an 8 base pair core sequence. See FIG. 1 of Sauer, B., Current Opinion in Biotechnology 5:521-527 (1994). Other examples of recognition sequences are the attB, attP, attL, and attR sequences which are recognized by the integrase of bacteriophage lambda. AttB is an approximately 25 base pair sequence containing two 9 base pair core-type Int binding sites and a 7 base pair overlap region. attP is an approximately 240 base pair sequence containing core-type Int binding sites and arm-type Int binding sites as well as sites for auxiliary proteins IIIF, FIS, and Xis. See Landy, Current Opinion in Biotechnology 3:699-707 (1993).

The term "Recombinase" refers to an enzyme which catalyzes the exchange of DNA segments at specific recombination sites.

The term "Recombinational Cloning" refers to a method whereby segments of DNA molecules are exchanged, inserted, replaced, substituted or modified, in vitro or in vivo.

The term "Recombination proteins" refers to excisive or integrative proteins, enzymes, co-factors or associated proteins that are involved in recombination reactions involving one or more recombination sites. See, Landy (1994), infra.

The term "Repression cassette" refers to a DNA segment that contains a repressor of a Selectable marker present in the subcloning vector.

The term "Scar" refers to extra DNA sequences that are left as part of a polynucleotide construct that are an unavoidable consequence of the construction method rather than being incorporated because of their desirable functional properties. For example recombinases, integrases and restriction endonucleases often have recognition sequences that remain within the sequence of a polynucleotide that is constructed using the action of said recombinases, integrases and restriction endonucleases. The term "Scar Size" refers to the length of the extra DNA sequences. For example a scar size of 34 base pairs is left in a construct with a recognition sequence for Cre recombinase, a scar size of 25 base pairs is added on when attB integrase is used. Scars can interfere with the functions of other sequence elements within the construct.

The term "Selectable marker" refers to a DNA segment that allows one to select for or against a molecule or a cell that contains it, often under particular conditions. These markers can encode an activity, such as, but not limited to, production of RNA, peptide, or protein, or can provide a binding site for RNA, peptides, proteins, inorganic and organic compounds or compositions. Examples of Selectable markers include but are not limited to: (1) DNA segments that encode products which provide resistance against otherwise toxic compounds (e.g., antibiotics); (2) DNA segments that encode products which are otherwise lacking in the recipient cell (e.g., tRNA genes, auxotrophic markers); (3) DNA segments that encode products which suppress the activity of a gene product; (4) DNA segments that encode products which can be readily identified (e.g., phenotypic markers such as beta-galactosidase, green fluorescent protein (GFP), and cell surface proteins); (5) DNA segments that bind products which are otherwise detrimental to cell survival and/or function; (6) DNA segments that otherwise inhibit the activity of any of the DNA segments described in Nos. 1-5 above (e.g., antisense oligonucleotides); (7) DNA segments that bind products that modify a substrate (e.g. restriction endonucleases); (8) DNA segments that can be used to isolate a desired molecule (e.g. specific protein binding sites); (9) DNA segments that encode a specific nucleotide sequence which can be otherwise non-functional (e.g., for PCR amplification of subpopulations of molecules); and/or (10) DNA segments, which when absent, directly or indirectly confer sensitivity to particular compounds.

The term "Counter Selectable Marker" refers to a DNA sequence that confers a selective disadvantage upon a host cell. Examples of counter-selectable markers include sacB, rpsL, tetAR, pheS, thyA, gata-1, ccdB, kid and barnase (Bernard, 1995, Journal/Gene, 162: 159-160; Bernard et al., 1994. Journal/Gene, 148: 71-74; Gabant et al., 1997, Journal/Biotechniques, 23: 938-941; Gababt et al., 1998, Journal/Gene, 207: 87-92; Gababt et al., 2000, Journal/Biotechniques, 28: 784-788; Galvao and de Lorenzo, 2005, Journa/Appl Environ Microbiol, 71: 883-892; Hartzog et al., 2005, Journal/Yeat, 22:789-798; Knipfer et al., 1997, Journal/Plasmid, 37: 129-140; Reyrat et al., 1998, Journal/Infect Immun, 66: 4011-4017; Soderholm et al., 2001, Journal/Biotechniques, 31: 306-310, 312; Tamura et al., 2005, Journal/Appl Environ Microbiol, 71: 587-590; Yazynin et al., 1999, Journal/FEBS Lett, 452: 351-354). Counter-selectable markers often confer their selective disadvantage in specific contexts. For example they may confer sensitivity to compounds that can be added to the environment of the host cell, or they may kill a host with one genotype but not kill a host with a different genotype. Conditions which do not confer a selective disadvantage upon a cell carrying a counter-selectable marker are described as "permissive". Conditions which do confer a selective disadvantage upon a cell carrying a counter-selectable marker are described as "restrictive".

The term "Selection scheme" refers to any method which allows selection, enrichment, or identification of a desired Product or Product(s) from a mixture containing the Insert Donor, Vector Donor, and/or any intermediates, (e.g. a Cointegrate) Byproducts. The selection schemes of one preferred embodiment have at least two components that are either linked or unlinked during recombinational cloning. One component is a Selectable marker. The other component controls the expression in vitro or in vivo of the Selectable marker, or survival of the cell harboring the plasmid carrying the Selectable marker. Generally, this controlling element will be a repressor or inducer of the Selectable marker, but other means for controlling expression of the Selectable marker can be used. Whether a repressor or activator is used will depend on whether the marker is for a positive or negative selection, and the exact arrangement of the various DNA segments, as will be readily apparent to those skilled in the art. A preferred requirement is that the selection scheme results in selection of or enrichment for only one or more desired Products. As defined herein, to select for a DNA molecule includes (a) selecting or enriching for the presence of the desired DNA molecule, and (b) selecting or enriching against the presence of DNA molecules that are not the desired DNA molecule.

Examples of such toxic gene products are well known in the art, and include, but are not limited to, restriction endonucleases (e.g., DpnI) and genes that kill hosts in the absence of a suppressing function, e.g., kicB. A toxic gene can alternatively be selectable in vitro, e.g., a restriction site.

The term "selectable protein" refers to a protein that provides a physical, chemical or biological method for selecting cells on the basis of how much of the selectable protein is expressed.

The term "translation" refers to the process by which a polypeptide is synthesized by a ribosome 'reading' the sequence of a polynucleotide.

The term "typeIIs restriction enzyme" refers to any restriction enzyme that cleaves DNA at a defined distance outside its recognition sequence, and whose recognition sequence is non-palindromic.

The term "Vector" or "DNA Vector" refers to a DNA sequence that is used to perform a "carrying" function for another polynucleotide. For example vectors are often used to allow a polynucleotide to be propagated within a living cell. The vector comprises a first typeIIs restriction site and a second typeIIs restriction site, wherein cleavage of said vector with said first and second typeIIs restriction enzymes produces a first polynucleotide vector fragment, referred to herein as a "vector fragment", which comprises a selectable marker but lacks said first and second typeIIs restriction sites, and a second polynucleotide fragment, referred to herein as a "stuffer fragment."

When one overhang on one nucleic acid is said to ligate to another overhang on another nucleic acid what is meant is that in the course of a ligation reaction the overhangs anneal leaving nicks sealed by the ligase thus joining the nucleic acids.

7.1.1 Advantages of Using Multiple TypeIIs Enzymes Simultaneously

We have developed a method for joining multiple polynucleotides in a single reaction with high efficiency. The method uses two different type IIs restriction enzymes that produce different length single stranded DNA overhangs when they cleave DNA. DNA ligases will ligate DNA overhangs with mismatched sequences, although at a lower frequency than perfectly matched DNA. However they will not ligate DNA overhangs that are of different lengths, for example a 3 base single-stranded DNA overhang will not ligate with a 4 base single-stranded DNA overhang, regardless of the sequence. Thus the use of typeIIs restriction enzymes to produce single-stranded overhangs with different lengths provides greater specificity and improves the efficiency with which the correct DNA sequence is assembled.

In one example, the type IIs restriction endonuclease that produces a 3 base single-stranded DNA overhang is BspQI or SapI and the type IIs restriction endonuclease that produces a 4 base single-stranded DNA overhang is BsaI.

While current standard cloning methods based on the use of restriction enzymes and ligases are very versatile, they are not well suited for assembly of multiple DNA fragments in a single step. Recombination-based cloning methods have been developed that allow making constructs in a single reaction with great efficiency. However, such an approach still suffers major drawbacks, the fact that unwanted recombination sites are left at the cloning junctions. Other effective cloning methods that use type IIs restriction enzymes have been developed, for example Golden Gate cloning uses BsaI that overcomes many of the limitations of current cloning methods (Engler et al., 2008, 2009). One drawback to this method is that since BsaI generates 4 base single-stranded DNA overhangs, it may lead to scars within an ORF. Another drawback when using a single type IIs restriction enzyme for assembly of multiple polynucleotides, for example either BsaI or SapI (Emami et al. 2013, Fontiers in Plant Sci., vol 4, article 339) is lowered specificity.

A cloning method that uses a combination of two different typeIIs restriction endonucleases, one that leaves a 4 base single-stranded DNA overhang and the other a 3 base single-stranded DNA overhang is advantageous for joining multiple polynucleotides in a single reaction. First, it provides an additional level of specificity. 4 base single-stranded DNA overhangs will ligate with slightly mismatched 4 base single-stranded DNA overhangs, but never with any 3 base single-stranded DNA overhang. A second advantage is that 3 base single-stranded DNA overhangs work well for linking two ORF as a fusion protein or as a single transcriptional unit (e.g., separated by an IRES element). Both linkage as a fusion protein and as a single transcriptional unit have precise spacing requirements, which are most readily satisfied by 3 base overhangs contributing exactly one codon. Three base overhangs can provide, for example an initiating ATG codon (methionine) for an ORF or alanine (GCN) at the start of the ORF when for example, a secretion signal is present at the start of the ORF or; a stop codon (TGA or TAG or TAA) at the end of the ORF or a glycine codon (GGN) or alanine codon (GCN) at the end of the ORF such that it allows transcription of a C-terminal fusion, for example a fluorescent protein, an enzyme fusion, an affinity tag, a solubility tag, glutathione-S-transferase (GST), maltose binding protein (MBP), FLAG tag, V5 epitope, a c-myc epitope, a hemagglutinin A epitope, Streptavidin II, T7 tag, S-tag, DHFR tag, chitin binding domain, calmodulin binding domain, cellulose biding domain, T7 gene 10 tag, NusA tag, thioredoxin, SUMO, ubiquitin tags, SNAP tag, MCP tag, ACP tag, a peptide sequence that serves as the recognition and/or cleavage site for a sequence specific protease including but not limited to TEV protease, AcTEV, ProTEV, HRV3C protease, thrombin, Factor Xa, Prescission protease, genenase I, Enterokinase (enteropeptidase), Furin, Proteinase K, modified Trypsin, Endoproteinase GluC, Endoproteinase AspN, SUMO proteases, Immobilized subtilisin BPN, Tagzyme (DAPase). Spacing requirements are usually less precise between an ORF and a promoter, and thus can be accommodated with four nucleotide overhangs.

Therefore, generating 4 base single-stranded DNA overhangs to join at vector insert boundaries and 3 base single-stranded DNA overhangs to join within an ORF or single transcriptional unit combines the specificity of forcing ligation to proceed to generate the intended product while at the same time conforming to precise spacing requirements in forming ORFs or single transcriptional units from multiple ORF. Use of a 7-base pair non-palindromic recognition sequence, such as that of SapI provides another advantage that it occurs at a frequency of one in 8192 base pairs, and thus has reduced likehood of being in an insert by chance relative to cleavage sites of enzymes with shorter recognition sequences.

7.1.2 Various Reactions for Using Multiple TypeIIs Enzymes Simultaneously

One method for joining three or more polynucleotides comprises combining into a mixture a first, second and third polynucleotide, where each polynucleotide comprises two typeIIs restriction sites, and at least two polynucleotides comprise a first recognition sequence recognized by a first typeIIs enzyme that cleaves DNA to leave a first DNA overhang length and a second recognition sequence recognized by a second typeIIs enzyme that cleaves DNA to leave a second DNA overhang length wherein the first and second overhang length are different. The mixture further comprises the first and second typeIIs restriction enzyme and a DNA ligase, such that the typeIIs enzymes cleave the first, second and third polynucleotides and the DNA ligase joins the resulting single-stranded overhangs to produce a product polynucleotide with predetermined sequence. In some examples the first overhang length is 4 bases and the second overhang length is 3 bases. In some examples the first typeIIs restriction enzyme is BsaI and the second typeIIs restriction enzyme is BspQI or SapI. In some examples the first typeIIs restriction enzyme is selected from a group consisting of AarI, Acc36I, AceIII, AspBHI, Alw26I, BbvI, BcoDI, BsmAI, BsmFI, BbsI, BfuAI, BsaI, Bsa-HF, BsmBI, Btg2I, BmsI, BseXI, BsIFI, BsoMAI, Bst71I, BstMAI, BstV1I, BbvII, BpiI, BpuAI, Bso31I, BspTNI, BstV2I, BveI, Eco31I, Esp3I, FspEI, FokI, FaqI, LpnPI, LweI, MspJI, R9896, SfaNI, SgeI, SgrTI, and Sth132I. In some examples the second typeIIs restriction enzyme is selected from a group consisting of BspQI, Bst6I, EarI, Eam1104I, Ksp632I, LguI, PciSI, and SapI.

The product polynucleotide preferably lacks a recognition sequence for the first and second typeIIs restriction endonucleases. The first polynucleotide may be selected from the group consisting of vectors, expression vectors, plasmid vectors, cosmid vectors, artificial chromosomes, viral vectors, and adeno-associated viral vectors.

One of the polynucleotides may comprise sequence elements controlling or influencing expression of another of the polynucleotides. Elements controlling or influencing expression may include a transcriptional promoter including a bidirectional promoter or an enhancer or a terminator, an element that binds to a regulatory protein such as an activator or repressor of transcription, or an element that modulates the efficiency of initiation of translation such as a ribosome binding site or a Kozak consensus sequence or coupling elements that facilitate bicistronic expression, for example an internal ribosome entry site (IRES) or a cis-acting hydrolysable element (CHYSEL/2A) element. The activity of expression-regulating elements may be specific to a certain host or group of hosts, for example specific to bacterial hosts or mammalian hosts or insect hosts or plant hosts or yeast hosts.

One polynucleotide may comprise a counter-selectable marker. The counter-selectable marker may be selected from the group consisting of sacB, rpsL, tetAR, pheS, thyA, lacY, gata-1, ccdB, kid and barnase. One polynucleotide or the product polynucleotide may comprise a selectable marker, which may be an antibiotic resistant gene. The antibiotic resistant gene may be a gene selected from the group consisting of an ampicillin resistant gene, a kanamycin resistant gene, a chloramphenicol resistant gene, and a zeocin resistant gene.

The mixture is preferably incubated between 18° C. and 37° C. The mixture may be incubated for between 4 minutes and 24 hours, more preferably between 15 minutes and 60 minutes.

The second typeIIs restriction endonuclease is preferably selected from a group consisting of BspQI, Bst6I, EarI, Eam1104I, Ksp632I, LguI, PciSI, and SapI. The first typeIIs restriction endonuclease may be selected from a group consisting of AarI, Acc36I, AceIII, AspBHI, Alw26I, BbvI, BcoDI, BsmAI, BsmFI, BbsI, BfuAI, BsaI, Bsa-HF, BsmBI, Btg2I, BmsI, BseXI, BsIFI, BsoMAI, Bst71I, BstMAI, BstV1I, BbvII, BpiI, BpuAI, Bso31I, BspTNI, BstV2I, BveI, Eco31I, Esp3I, FspEI, FokI, FaqI, LpnPI, LweI, MspJI, R9896, SfaNI, SgeI, SgrTI, and Sth132I. The second typeIIs restriction endonuclease may be selected from a group consisting of AarI, Acc36I, AceIII, AspBHI, Alw26I, BbvI, BcoDI, BsmAI, BsmFI, BbsI, BfuAI, BsaI, Bsa-HF, BsmBI, Btg2I, BmsI, BseXI, BsIFI, BsoMAI, Bst71I, BstMAI, BstV1I, BbvII, BpiI, BpuAI, Bso31I, BspTNI, BstV2I, BveI, Eco31I, Esp3I, FspEI, FokI, FaqI, LpnPI, LweI, MspJI, R9896, SfaNI, SgeI, SgrTI, and Sth132I. The first typeIIs restriction endonuclease may be selected from a group consisting of BspQI, Bst6I, EarI, Eam1104I, Ksp632I, LguI, PciSI, and SapI.

The concentration of the first polynucleotide in the mixture may be between 0.1 pM and 100 nM, the concentration of the first polynucleotide in the mixture is preferably between 0.1 pM and 10 nM.

The concentration of the second, third and fourth polynucleotides in the mixture may be between 0.1 pM and 100 nM, the concentration of the second, third and fourth polynucleotides in the mixture may be between 1 pM and 10 nM, the concentration of the second, third and fourth polynucleotides in the mixture may be between 0.1 pM and 1 µM.

The concentration of the first and second typeIIs restriction endonuclease in the mixture may be each independently between 0.01 U/µl and 100 U/µl, the concentration of the first and second typeIIs restriction endonuclease in the mixture may be each independently between 0.1 U/µl and 10 U/µl, the concentration of the first and second typeIIs restriction endonuclease in the mixture may be each independently between 0.01 U/µl and 10 U/µl.

The concentration of the DNA ligase in the mixture may be between 1 U/µl and 400 U/µl, the concentration of the DNA ligase in the mixture may be between 1 U/µl and 40 U/µl, the concentration of the DNA ligase in the mixture may be between 1 U/µl and 4 U/µl.

A product polynucleotide may be produced by a method comprising transforming the product polynucleotide into a host cell, growing the host cell under conditions that favor the growth of host cells containing the selectable marker and, optionally, isolating the product polynucleotide from the host cell.

Product polynucleotide may be produced by incubating a mixture for a predetermined length of time, transforming the mixture into a host cell, and growing the host cell under conditions that select for the presence of a selectable marker.

Producing a product polynucleotide may comprise transforming the product polynucleotide into a host cell, growing the host cell under conditions that favor the growth of host cells containing the selectable marker and, optionally, isolating the product polynucleotide from the host cell.

7.1.3 Design of Polynucleotide Overhangs

Ends with broadly useful overhangs can be created on polynucleotides for use with many other partners. For example open reading frames all begin with a methionine codon (which is 5'-ATG-3') and end with a stop codon (5'-TAG-3', or 5'-TAA-3', or 5'-TGA-3'). Thus a polynucleotide encoding a polypeptide can always be created with a 5'-ATG-3' overhang at one end, and a 5'-CTA-3', or 5'-TTA-3', or 5'-TCA-3' overhang at the other end. Similarly, many bacterial and mammalian secretion leader peptides end with alanine, so open reading frames beginning with an alanine codon (which is 5'-GCC-3', or 5'-GCA-3', or 5'-GCT-3', or 5'-GCG-3') will be compatible with a plurality of polynucleotides each comprising a sequence encoding a bacterial or mammalian secretion signal. Similarly, a small amino acid such as glycine or alanine, is a useful part of a linker peptide because it reduces steric interference with two domains fused together, so open reading frames ending with an alanine codon (which is 5'-GCC-3', or 5'-GCA-3', or 5'-GCT-3', or 5'-GCG-3') or a glycine codon (which is 5'-GGC-3', or 5'-GGA-3', or 5'-GGT-3', or 5'-GGG-3') will be compatible with a plurality of polynucleotides each comprising a sequence encoding a C-terminal fusion such as glutathione-S-transferase (GST), maltose binding protein (MBP), FLAG tag, V5 epitope, a c-myc epitope, a hemagglutinin A epitope, Streptavidin II, T7 tag, S-tag, DHFR tag, chitin binding domain, calmodulin binding domain, cellulose biding domain, T7 gene 10 tag, NusA tag, thioredoxin, SUMO, ubiquitin tags, SNAP tag, MCP tag, ACP tag, a peptide sequence that serves as the recognition and/or cleavage site for a sequence specific protease. Such sequences include but are not limited to TEV protease, AcTEV, ProTEV, HRV3C protease, thrombin, Factor Xa, Prescission protease, genenase I, Enterokinase (enteropeptidase), Furin, Proteinase K, modified Trypsin, Endoproteinase GluC, Endoproteinase AspN, SUMO proteases, Immobilized subtilisin BPN, Tagzyme (DAPase).

Particularly useful polynucleotides for use in assembly of product polynucleotides for expression of two open reading frames may comprise elements for control of gene expression (including for example an enhancer, a promoter, an intron, a 5' UTR or an IRES) and a 5'-CAT-3' overhang at the 3' end to join to the 5'-ATG-3' overhang of a polynucleotide encoding an open reading frame.

Some preferred 4 base polynucleotide overhangs are 5'-CCCC-3', or 5'-TTTT-3', or 5'-GGGG-3' or 5'-AAAA-3'.

It is particularly important to avoid overhangs where the two ends of one polynucleotide can ligate with each other, since this would result in a circular DNA molecule that can transform a host cell, but which does not carry an insert. It is also preferable that the two ends of a polynucleotide should not be pseudo-complementary. That is, they should not be complementary even if T-G is considered also as a complementary base pair.

Furthermore it is also preferable that the polynucleotides can join only in one specific order, considering both complementary and pseudo-complementary bases. For example if a first polynucleotide has a 5'-CAT-3' overhang at its first end, to be complementary with a 5'-ATG-3' overhang at the first end of a second polynucleotide, the overhang at the second end of the second polynucleotide should be neither 5'-ATG-3', which is a perfect complement to 5'-CAT-3', nor 5'-GTG-3', because 5'-GTG-3' will complement 5'-CAT-3' with a T-G base pair. Either of these cases could result in the second end of the second polynucleotide ligating to the first end of the first polynucleotide instead of the intended joining of the first end of the first polynucleotide to the first end of the second polynucleotide, which would completely change the sequence of the product polynucleotide from the design sequence. The use of overhangs of different lengths reduces the likelihood of undesired end joining through pseudo-complementary base pairing, because overhangs of different lengths are not joined by DNA ligases.

The product polynucleotide preferably lacks recognition sites for the typeIIs restriction enzymes present in the mixture, and therefore is not digested. The original polynucleotides initially placed into the mixture comprise sites for the typeIIs restriction enzymes present in the mixture, wherein cleavage of the polynucleotide with the typeIIs restriction enzymes releases an insert fragment that lacks sites for the typeIIs restriction enzymes present in the mixture. Thus if the insert fragment ligates with other digestion products of the polynucleotides to reconstitute all or a part of the original polynucleotide, the polynucleotide will be digested again by the typeIIs restriction enzymes in the reaction to again produce the insert fragment. The mixture may comprise one or more polynucleotide fragments that have been pre-digested with one or more typeIIs restriction enzymes and optionally purified. This pre-digested and purified polynucleotide may comprise vector components such as a selectable marker or an origin of replication. It may further comprise elements regulating expression in an expression host, such as an enhancer, a promoter, an intron or a 5' UTR.

For example, a product polynucleotide can be formed in a single reaction mixture comprising: A vector; two or more polynucleotides comprising genetic elements; two typeIIs restriction enzymes that releases insert fragments from the polynucleotides, and a vector fragment from the vector; a DNA ligase.

Alternatively a product polynucleotide can be formed in a single reaction mixture comprising: A vector fragment; two or more polynucleotides comprising genetic elements; two typeIIs restriction enzymes that releases insert fragments from the polynucleotides, and a vector fragment from the vector; a DNA ligase.

The polynucleotides may be linear fragments of DNA, or closed circle of DNA. The polynucleotides may be produced by DNA synthesis, or may be produced by PCR amplification from a template. PCR amplification may be used to add typeIIs restriction sites and sequences that will produce an insert fragment with overhangs, one end that is compatible with one end of a vector fragment and one end compatible with other insert fragments or the other end of the vector fragment following digestion of the polynucleotides with typeIIs restriction enzymes.

The product polynucleotide typically comprises a selectable marker, which may be provided by one of the original polynucleotides, or may be provided in part by two or more of the original polynucleotides. Examples of selectable markers include: (1) DNA segments that encode products which provide resistance against otherwise toxic compounds (e.g., antibiotics); (2) DNA segments that encode products which are otherwise lacking in the recipient cell (e.g., tRNA genes, auxotrophic markers); (3) DNA segments that encode products which suppress the activity of a gene product; (4) DNA segments that encode products which can be readily identified (e.g., phenotypic markers such as beta.-galactosidase, green fluorescent protein (GFP), and cell surface proteins); (5) DNA segments that bind products which are otherwise detrimental to cell survival and/or function; (6) DNA segments that otherwise inhibit the activity of any of the DNA segments described in Nos. 1-5 above (e.g., antisense oligonucleotides); (7) DNA segments that bind products that modify a substrate (e.g. restriction endonucleases); (8) DNA segments that can be used to isolate a desired molecule (e.g. specific protein binding sites); (9) DNA segments that encode a specific nucleotide sequence which can be otherwise non-functional (e.g., for PCR amplification of subpopulations of molecules); and/or (10) DNA segments, which when absent, directly or indirectly confer sensitivity to particular compounds. In some embodiments the selectable marker is an antibiotic, for example selected from but not limited to ampicillin or kanamycin or chloramphenicol or zeocin.

The product polynucleotide may be obtained by transforming the single reaction mixture into a host cell. For transformation into a host cell it may be advantageous for the product polynucleotide to be circular, in some embodiments the product polynucleotide may be linear.

When a single reaction mixture is transformed into a host cell, in addition to the product polynucleotide the reaction may contain unreacted polynucleotides, digestion products and partially ligated products. It is advantageous to prepare single reaction mixtures such that the product polynucleotide enjoys a selective advantage in the host relative to the other polynucleotides in the mixture. This can be accomplished in a number of ways.

For example, if the vector fragment and the product polynucleotide comprise a first selectable marker and the polynucleotides comprise a second selectable marker, it is preferable that the first and second selectable markers are different. After transformation of the mixture into the host cell, it is advantageous to grow the host cell under conditions where the first selectable marker provides a growth advantage, but the second selectable marker does not.

The polynucleotides may additionally comprise a counter-selectable marker to prevent propagation of the polynucleotides within a host cell. In certain embodiments, the counter-selectable marker is sacB, rpsL, tetAR, pheS, thyA, lacY, gata-1, ccdB, kid or barnase. In some embodiments said polynucleotide further comprises a double-stranded DNA break, or a dephosphorylated double-stranded DNA break, or a counter-selectable marker within said discard fragment sequence, in some embodiments said counter-selectable marker is sacB, rpsL, tetAR, pheS, thyA, lacY, gata-1, ccdB, kid or barnase. In some embodiments said mixture is transformed into a host cell that is grown under conditions that are restrictive for growth of cells containing a counter-selectable marker, thereby preventing the growth of cells containing DNA comprising said stuffer fragment or said discard fragment. In certain embodiments, the counter-selectable marker is rpsL that confers sensitivity to streptomycin. In certain embodiments, the counter-selectable marker is pheS that confers sensitivity to p-chlorophenylalanine, a toxic form of amino acid phenylalanine.

For example, if the polynucleotide comprises a counter-selectable marker that is not present or not functional in the insert fragment sequence, then cells that have been transformed with the polynucleotide may be selected against by growing the transformed cells under conditions that are restrictive for the counter-selectable marker. Useful counter-selectable markers include sacB, rpsL, tetAR, pheS, thyA, lacY, gata-1, ccdB, kid or barnase. If the polynucleotide comprises a counter-selectable marker, then it is possible to use the same selectable marker in both the polynucleotide and the product polynucleotide, and to select for cells that are carrying only the product polynucleotide by selecting for the selectable marker and against the counter-selectable marker.

A vector may also comprise a counter-selectable marker that is not present or not functional in the vector fragment sequence, or in the product polynucleotide. In this case, it may not be necessary to use vector fragment in a single reaction, but untreated vector may be used. In this case, cells that have been transformed with the vector may be selected against by growing the transformed cells under conditions that are restrictive for the counter-selectable marker. Thus only host cells carrying vector from which the stuffer fragment has been excised and into which an insert fragment has been ligated, will survive. Useful counter-selectable markers include sacB, rpsL, tetAR, pheS, thyA, lacY, gata-1, ccdB, kid or barnase. A vector counter-selectable marker may be the same or different from a polynucleotide counter-selectable marker.

Under appropriate growth conditions, a counter-selectable gene promotes the death of the microorganism harboring it, hence allowing transformants that have retained the counter-selectable marker to be eliminated in the presence of the counter-selective compound. Examples of counter-selectable markers include rpsL genes that make cells sensitive to streptomycin; pheS genes that encodes the α subunits of Phe-tRNA synthetase, which renders bacteria sensitive to the phenylalanine analog p-chlorophenylalanine; sacB genes that encodes levansucrase, an enzyme that converts sucrose to levans which are harmful to bacteria; thyA genes which encodes thymidylate synthetase, which confers sensitivity to trimethoprim and related compounds; lacy genes that encode lactose permease, which renders bacteria sensitive to t-o-nitrophenyl-b-D-galactopyranoside; gata-1 genes that encodes zinc finger DNA-binding proteins which inhibit initiation of bacterial replication; and ccdB genes which encode a cell-killing protein which is a potent poison of bacterial gyrase.

Preferred mixtures of polynucleotides, vector or vector fragment, typeIIs restriction endonucleases and ligase for forming product polynucleotides comprise vector or vector fragment concentrations between 0.01 pM and 1 µM, more preferred mixtures contain vector or vector fragment concentrations between 0.1 pM and 100 nM, more preferred mixtures contain vector or vector fragment concentrations between 1 pM and 10 nM. Preferred mixtures comprise polynucleotide concentrations between 0.01 pM and 1 µM, more preferred mixtures contain polynucleotide concentrations between 0.1 pM and 100 nM, more preferred mixtures contain polynucleotide concentrations between 1 pM and 10 nM. Preferred mixtures comprise restriction endonuclease concentrations between 0.01 U/µl and 100 Uµl, more preferred mixtures contain endonuclease concentrations between 0.1 U/µl and 10 U/µl, more preferred mixtures contain endonuclease concentrations between 0.1 U/µl and 1 U/µl. Preferred mixtures comprise DNA ligase concentrations between 1 U/µl and 400 U/µl, more preferred mixtures contain DNA ligase concentrations between 1 U/µl and 40 U/µl, more preferred mixtures contain DNA ligase concentrations between 1 U/µl and 4 U/µl.

The restriction endonucleases(s) can be combined with the DNA ligase(s) in a single tube prior to use in a single reaction. This allows an optimal ratio of the two enzymes to be added easily. It also prevents inadvertent omission of one of the enzymes from a reaction. In another particular embodiment, the buffer(s), restriction endonuclease(s) and the ligase(s) are pre-mixed and retain each individual component's desired function. Providing these two reagents in an easy-to-use form is advantageous to the user, and a preferred embodiment.

7.1.4 Three-Way Assemblies

The methods and compositions described herein are particularly advantageous for assembly of multiple polynucleotides, and for producing product polynucleotides with precise and specific juxtapositions of sequence elements that regulate gene expression (such as enhancers, promoters, introns, 5' untranslated regions, 3' untranslated regions, post-transcriptional responsive elements, polyadenylation sequences, matrix attachment regions and genetic insulators) with genes to be expressed such as open reading frames. These methods also allow two parts of an open reading frame to be seamlessly fused to produce a gene encoding a single polypeptide.

In one embodiment of the invention, sequences that confer properties that may include a selectable marker, an origin of replication and regulation of gene expression may be present on a first polynucleotide which serves as the vector. A second and third polynucleotide collectively encodes a single polypeptide. The vector comprises two sites for a first typeIIs enzyme and the second and third polynucleotide each comprise one site for said first typeIIs enzyme and one site for a second typeIIs enzyme. The first and second typeIIs enzymes leave overhangs of different lengths. In some examples the first overhang length is 4 bases and the second overhang length is 3 bases. In some examples the first typeIIs restriction enzyme is BsaI and the second typeIIs restriction enzyme is BspQI or SapI. Digestion of all 3 polynucleotides with both typeIIs enzymes and ligation of the digestion products causes the 3 polynucleotides to assemble into a product polynucleotide comprising a selectable marker, an open reading frame and element(s) that controls the expression of the open reading frame. Such a scheme is shown in FIG. 1.

This efficient assembly scheme may be useful to provide a large number of product polynucleotides from a much smaller number of initial polynucleotides. For example ten vectors each comprising a different set of elements for regulation of expression and ten versions of the second polynucleotide comprising ten different secretion signals may be combined with a third polynucleotide encoding a secretable protein to produce 100 different combinations of regulatory elements and secretion signals precisely juxtaposed with the open reading frame. Alternatively the second polynucleotide may comprise an open reading frame encoding a polypeptide that is to be fused to a target polypeptide to localize, monitor, solubilize or purify the polypeptide, for example glutathione-S-transferase (GST), maltose binding protein (MBP), FLAG tag, V5 epitope, a c-myc epitope, a hemagglutinin A epitope, Streptavidin II, T7 tag, S-tag, DHFR tag, chitin binding domain, calmodulin binding domain, cellulose biding domain, T7 gene 10 tag, NusA tag, thioredoxin, SUMO, ubiquitin tags, SNAP tag, MCP tag or an ACP tag. The method described herein enables the efficient creation of many different polynucleotides for identification of combinations that possess desired properties.

7.1.5 Four-Way Assemblies

The methods and compositions described herein are also particularly advantageous for producing product polynucleotides capable of expressing two different polypetides. As well as the two polynucleotides expressing different polypeptides, the methods use a vector and optionally a spacer nucleic acid. The vector, sometimes referred to as first polynucleotide, can include or encode elements, such as a selectable marker, an origin of replication and one or more elements for regulation of gene expression. A second and third polynucleotide each encodes a different polypeptide. A fourth polynucleotide comprises one or more sequence elements that regulate gene expression, and/or can encode a peptide to serve as a linker or labelling tag between the first and second polypeptides. The vector comprises two sites for a first typeIIs enzyme; the second and third polynucleotide each comprise one site for said first typeIIs enzyme and one site for a second typeIIs enzyme; the fourth polynucleotide comprises two sites for the second typeIIs enzyme. The first and second typeIIs enzymes leave overhangs of different lengths. The first overhang length is preferably 4 bases and the second overhang length is preferably 3 bases. In a preferred combination of enzymes, the first typeIIs restriction enzyme is BsaI and the second typeIIs restriction enzyme is BspQI or SapI. Digestion of all 4 polynucleotides with both typeIIs enzymes and ligation of the digestion products causes the 4 polynucleotides to assemble into a product polynucleotide comprising a selectable marker and two open reading frames operably linked to sequence elements that control the expression of the encoded polypeptides. Such a scheme is shown in FIG. 2.

Cleavage of the vector or first polynucleotide by the first type IIs enzyme generates a vector fragment. Cleavage of the second and fourth polynucleotides by the first and second type IIs enzymes generates first and second insert nucleic acids and cleavage of the third polynucleotide generates a spacer nucleic acid.

The vector fragments, first and second inserts and spacer nucleic acid can be ligated into a vector. The disposition of four and three base overhangs among the four nucleic acids drives ligation so that the nucleic acid ligate in the desired order to form a vector in which the spacer fragment is flanked by the first and second inserts, which are joined through the vector fragments. In this orientation, the first insert can be placed in operable linkage with regulatory element(s) in the vector fragment and the second insert, or for a single transcriptional unit, both the first and second inserts, can be placed in operable linkage with regulatory element(s) in the spacer. Alternatively, three base overhangs on the first and second insert nucleic acids can be ligated to each other without a spacer nucleic acid with the four base overhangs ligating to the vector fragment.

The three base overhangs on the first and second insert nucleic acids and optional spacer nucleic acids can provide an initiator codon, a termination codon, or a linking amino acid, particularly glycine or alanine between domains of a fusion protein. For example, joining of the three base overhang of the first insert nucleic acid and the three base overhang of the spacer generates a stop codon for the polypeptide encoded by the first insert nucleic acid. Joining of the three base overhang of the second insert nucleic acid and three base overhang of the spacer generates an initiation codon for the polypeptide encoded by the second insert nucleic acid. Joining of the three base overhang of the first insert nucleic acid and the three base overhang of the second insert nucleic acid (i.e., without a spacer nucleic acid) forms a glycine or alanine codon expressed as a glycine or alanine between the first and second polypeptides in a fusion protein. In some methods, the spacer encodes a peptide and the joining of the three base overhang of the first insert nucleic acid and a three base overhang of the spacer forms a glycine or alanine codon expressed as a glycine or alanine between the first polypeptide and the peptide encoded by the spacer. In other methods when the spacer encodes a peptide, the joining of the three base overhang of the second insert nucleic acid and a three base overhang of the spacer forms a glycine or alanine codon expressed as a glycine or alanine between second polypeptide and the peptide encoded by the spacer.

The first and fourth polynucleotide or vector fragment and spacer nucleic acid can be supplied together as a kit for combination with user supplied insert nucleic acids. Optionally, multiple versions of first and four polynucleotides or vector fragment and spacer nucleic acid derived therefrom can be supplied containing, for example different version of regulatory signals. Any or all of the cleavages necessary to generate vector fragment, first and second insert nucleic acids and the spacer nucleic acid can be performed before or at the same time as the ligation. Preferably, the type IIs recognition sequences are generated outside the vector fragment, first and second insert nucleic acid and spacer nucleic acid, so that the desired product is not subject to cleavage by the first and second type IIs enzymes.

This efficient assembly scheme may be useful to provide a large number of product polynucleotides representing permutations of a much smaller number of initial polynucleotides. For example to express antibodies efficiently it is frequently beneficial to control the ratio of expression between the heavy and light chains. Thus if the second and third polynucleotides comprise sequences encoding the heavy and light chains of an antibody, the vector can include one or more sequence elements that control expression of one of the chains and the fourth polynucleotide can include one or more sequence elements that control expression of the other chain Many different combinations can be created in which different control elements are juxtaposed with the different antibody chains, thereby simplifying identification of high performing polynucleotide configurations.

The fourth polynucleotide may comprise elements such as polyadenylation sequences, transcriptional terminators, genetic insulators, enhancers, promoters and introns to allow the independent transcription of the two polypeptides. Elements controlling or influencing expression may include a transcriptional promoter including a bidirectional promoter or an enhancer or a intron or a terminator, an element that binds to a regulatory protein such as an activator or repressor of transcription, or an insulator element(s) that prevents spread of heterochromatin or promoter interference, or a RNA processing and export element, or an element that modulates the efficiency of initiation of translation such as a ribosome binding site or a Kozak consensus sequence or an internal ribosome entry site (IRES) or a cis-acting hydrolysable element (CHYSEL/2A). For example promoters may be selected from any mammalian or avian species including but not limited to human, rat, mice, chicken and Chinese hamster, the CMV promoter, EF1a promoter, actin promoter, SV40 promoter, PGK promoter, GAPDH promoter, ubiquitin promoter and more; enhancer elements may be selected from CMV immediate early enhancer, EF1a enhancer, adenoviral major late protein enhancer, SV40 enhancer and more; an intron may be selected from CMV intron A, CMV intron B, CMV intron C, EF1a intron, GAPDH intron, adenoviral major late protein intron and more; 5' untranslated regions (5' UTRs) from any mammalian or avian species including but not limited to human, rat, mice, chicken and Chinese hamster; polyadenylation signals may be selected from bovine growth hormone (BGH), human growth hormone (HGH), human or rabbit beta globin, viral polyadenylation signals including those from SV40 or herpes simplex virus and more; terminators from gastrin and more; insulators selected from HS4, UCOE and more.

The fourth polynucleotide may comprise translational coupling elements such as internal ribosome entry sites (IRESes) to couple expression of the two polypeptides from a single transcript.

In some embodiments, one of the ORFs can be a selectable marker. In some embodiments, one of the ORFs can be a reporter, for example a fluorescent protein or an enzyme, for example secreted alkaline phosphatase (SEAP).

7.1.6 Vector Compositions

TypeIIs restriction endonucleases recognize asymmetric DNA sequences and cleave both DNA strands at fixed positions, typically several base pairs away from the recognition sites. This property makes typeIIs restriction endonucleases particularly useful for assembling DNA fragments, where fragments with matching type IIs-generated ends are annealed and ligated, leaving an assembled DNA product without restriction recognition sequence scars at the ligation junctions. Type IIs restriction endonucleases that recognize non-palindromic sequences of 5, 6 or 7 base pairs, are found at an average frequency of one in 512, 2048 or 8192 base pairs respectively. It is therefore, relatively easy to identify typeIIs restriction endonucleases that do not cut inside a typical gene-sized DNA fragment.

A vector can be constructed to permit cloning using typeIIs restriction endonucleases and ligase by incorporating a staffer flanked by typeIIs restriction sites into a vector comprising a selectable marker. It is advantageous to place typeIIs restriction sites in a vector such that cleavage of the vector with one or more typeIIs restriction enzymes yields a vector fragment with ends that are not compatible with each other. This design imposes directionality upon the ligation of one or more insert fragments with the vector fragment; it also prevents the vector fragment from ligating with itself. In preferred embodiments the vector fragment ends are also not pseudo-compatible with each other; that is they do not anneal with each other by forming at least one non-standard Watson-Crick base pair (i.e., T or U with G) in a way that can be joined by a DNA ligase with reasonable efficiency.

Any vector can be converted to a vector capable of supporting a one-step multi fragment typeIIs restriction cloning. This can be done by designing and synthesizing a nucleic acid sequence for a cloning cassette as described herein, then cloning that cassette into the vector to be converted. In some embodiments the cloning cassette comprises a counter-selectable marker flanked by typeIIs restriction sites, wherein the typeIIs restriction sites are not present in the other parts of the vector to be converted. Such design and synthesis methods are well known in the art. The conversion of vectors to allow 1-step type IIs cloning is expressly contemplated.

Of course, one of skill in the art will recognize that alternative methods can be used to construct a vector suitable for use in the methods, compositions, and kits described herein. For example, oligonucleotides containing appropriate Type IIs recognition sequences can be synthesized and introduced into the vector using standard techniques, or a counter-selectable marker may be amplified by the polymerase chain reaction.

Because typeIIs restriction endonucleases cleave DNA outside their target sequences, they generate overhangs whose sequences are independent of their recognition sequence. Thus the product polynucleotide may contain a sequence derived from the vector fragment that is precisely juxtaposed with a sequence derived from the insert fragments. In some embodiments a product polynucleotide comprises an element that controls or influences expression that is derived from one of the fragments, placed precisely in relation to an element to be expressed that is derived from the other fragment. Elements controlling or influencing expression may include a transcriptional promoter or an enhancer or a terminator, an element that binds to a regulatory protein such as an activator or repressor of transcription, or an element that modulates the efficiency of initiation of translation such as a ribosome binding site or a Kozak consensus sequence or an internal ribosome entry site (IRES). The activity of expression-regulating elements may be specific to a certain host or group of hosts, for example specific to bacterial hosts or mammalian hosts or insect hosts or plant hosts or yeast hosts.

In some embodiments a product polynucleotide comprises two elements encoding polypeptides, one derived from the insert fragment and the other derived from the vector fragment, wherein the two elements are juxtaposed such that they encode a single contiguous polypeptide without any extraneous sequence derived from residual restriction recognition sequences. In some embodiments the contiguous polypeptide comprises a sequence that is partly encoded by a the vector fragment, and that confers a property affecting solubility, stability, proper folding, improved yields, localization, color or fluorescence of a protein, or affinity of a protein for a substrate, or a characteristic that facilitates purification or tracking of a protein in a cell.

In some embodiments, the vector comprises sequences encoding fusion tags, wherein the fusion tags are fused either to the N- or C-terminus of an open reading frame (ORF) encoded in the product polynucleotide by sequences derived from the insert fragment. Fusion tags can facilitate detection and/or purification of a protein. For example, use of poly-histidine tags are well known in the art and are used for detection of expression using antibodies raised against poly-histidine, they can also facilitate affinity purification using a $Ni^{2+}$ or $Co^{2+}$ affinity columns Poly-histidine tags have an affinity for nickel or cobalt ions which are coordinate covalently bonded with a chelator for purposes of solid medium entrapment. In some embodiments the vector comprises a sequence that encodes a polyhistidine tag comprising from about two to ten contiguous histidine residues (e.g., two, three, four, five, six, seven, eight, nine or ten contiguous histidine residues). The tag can also be a peptide tag which binds nickel ions, as well as other metal ions (e.g., copper ion), and can be used for metal chelate affinity chromatography. Examples of such tags include peptides having the formula: $R_1$-(His-X)$_n$—$R_2$, wherein (His-X) represents a metal chelating peptide and n is a number between two through ten (e.g., two, three, four, five, six, seven, eight, nine or ten), and X is an amino acid selected from the group consisting of alanine, arginine, aspartic acid, asparagines, cysteine, glutamic acid, glutamine, glycine, histidine, isoleucine, leucine, lysine, methionine, phenylalanine, proline, serine, threonine, tryptophan, tyrosine, and valine. Further $R_2$ may be a polypeptide that is covalently linked to the metal chelating peptide and $R_1$ may be either a hydrogen or one or more (e.g., one, two, three, four, five, six, seven, eight, nine, ten, twenty, thirty, fifty, sixty or more) amino acid residues. In addition $R_1$ may be a polypeptide which is covalently linked to the metal chelating peptide and $R_2$ may be either a hydrogen or one or more (e.g., one, two, three, four, five, six, seven, eight, nine, ten, twenty, thirty, fifty, sixty or more) amino acid residues. Tags of this nature are described in U.S. Pat. No. 5,594,115.

In some embodiments, the vector comprises sequences encoding other fusion tags including but not limited to glutathione-S-transferase (GST), maltose binding protein (MBP), FLAG tag, V5 epitope, a c-myc epitope, a hemagglutinin A epitope, Streptavidin II, T7 tag, S-tag, DHFR tag, chitin binding domain, calmodulin binding domain, cellulose biding domain, T7 gene 10 tag, NusA tag, thioredoxin, SUMO, ubiquitin tags, SNAP tag, MCP tag, ACP tag. In some embodiments, the vector comprises sequences encoding a peptide sequence that serves as the recognition and/or cleavage site for a sequence specific protease. Such sequences include but are not limited to TEV protease, AcTEV, ProTEV, HRV3C protease, thrombin, Factor Xa, Prescission protease, genenase I, Enterokinase (enteropeptidase), Furin, Proteinase K, modified Trypsin, Endoproteinase GluC, Endoproteinase AspN, SUMO proteases, Immobilized subtilisin BPN, Tagzyme (DAPase).

In certain embodiments, a vector encodes a cell compartmentalization domain, such as a plasma membrane localization domain, a nuclear localization signal, a mitochondrial membrane localization signal, an endoplasmic reticulum localization signal, or a protein transduction domain such as the human immunodeficiency virus TAT protein transduction domain, which can facilitate translocation of a peptide linked thereto into a cell (see Schwarze et al., Science 285: 1569-1572, 1999; Derossi et al., J. Biol. Chem. 271:18188, 1996; Hancock et al., EMBO J. 10:4033-4039, 1991; Buss et al., Mol. Cell. Biol. 8:3960-3963, 1988; U.S. Pat. No. 5,776,689). Such a domain can be useful to target a fusion polypeptide compressing the domain and a polypeptide encoded by an insert fragment, to a particular compartment in the cell, or for secretion from or entry into a cell.

In some embodiments the contiguous polypeptide comprises a 2A peptide or a CHYSEL sequence which allow the expression of more than one polypeptide to be driven by a single promoter sequence in eukaryotic cells. A 2A peptide sequence or a CHYSEL site causes a eukaryotic ribosome to release the growing polypeptide chain, but continue translating, thereby giving rise to two separate polypeptides from a single translating ribosome. An expression cassette using a 2A peptide or a CHYSEL coupling element comprises a promoter, a nucleic acid sequence encoding a first polypeptide, a nucleic acid sequence that encodes a 2A peptide or a CHYSEL peptide and a second nucleic acid sequence encoding a second polypeptide. In some embodiments the first or second polypeptide may comprise a selectable protein including any chromogenic or fluorescent protein. One functional order of elements is promoter then selectable protein then 2A peptide or CHYSEL peptide then open reading frame of interest. Another functional order of elements is promoter then open reading frame of interest then 2A peptide or CHYSEL peptide then selectable protein.

In certain embodiments, the vector is a cloning vector or an expression vector. In some embodiments the vector comprises a eukaryotic origin of replication. In some embodiments, the vector is a plasmid vector, a cosmid vector, an artificial chromosome (for example a bacterial artificial chromosome, a yeast artificial chromosome or a mammalian artificial chromosome), a viral vector such as a bacteriophage, baculovirus, retrovirus, lentivirus, adenovirus, Vaccinia virus, semliki forest virus or adeno-associated virus vector, all of which are well known and can be purchased from commercial sources (Promega, Madison Wis.; Stratagene, La Jolla Calif.; GIBCO/BRL. Gaithesburg Md.). Viral expression vectors can be particularly useful where a method is practiced for the purpose of generating a recombinant nucleic acid molecule that is to be introduced into a cell, particularly a cell in a subject. Viral vectors provide the advantage that they can infect host cells with relatively high efficiency and can infect specific cell types or can be modified to infect particular cells in a host.

In some embodiments the vector is a viral vector developed for use in a particular host system; for example a baculovirus vector which infects insect cells; a retroviral vector, a lentiviral vector based on the human immunodeficiency virus (HIV), an adenovirus vector, an adeno-associated virus (AAV) vector, a herpesvirus vector, or a Vaccinia virus vector which infects mammalian cells (Miller and Rosman, Biotechniques 7:980-990, 1992; Anderson et al., Nature 392:25-30 Suppl., 1998; Verma and Somia, Nature 389:239-242, 1997; Wilson, New Engl. J. Med. 334:1185-1187, 1996, each of which is incorporated herein by reference). For example, a viral vector based on an HIV can be used to infect T cells, a viral vector based on an adenovirus can be used, for example, to infect respiratory epithelial cells, and a viral vector based on herpesvirus can be used to infect neuronal cells. Other vectors, such as AAV vectors can have a greater host cell range and, therefore, can be used to infect various cell types, although viral or non-viral vectors can also be modified with specific receptors or ligands to alter target specificity through receptor mediated events.

In some embodiments the vector comprises a transcriptional expression control element that is a promoter from a virus including cytomegalovirus, Miloney leukemia virus and herpes virus; or a promoter from a gene encoding metallothionein, skeletal actin, phosphoenolpyruvate carboxylase, phosphoglycerate, dihydrofolate reductase, or thymidine kinase; or a promoter from a viral long terminal repeat (LTR) such as Rous sarcoma virus LTR; or a constitutive enhancer such as an immunoglobin enhancer; or an inducible enhancer such as an SV40 enhancer. A metallothionein promoter is a constitutively active promoter that can be induced to a higher level of expression upon exposure to a metal ion such as copper, nickel or cadmium ion. A tetracycline (tet) inducible promoter is an example of a promoter that is induced upon exposure to tetracycline, or a tetracycline analog, but is otherwise inactive.

In some embodiments the vector comprises a tissue specific transcriptional expression control element. Tissue specific promoters are active in specific type of cells or tissues such as B cells, monocytic cells, leukocytes, macrophages, muscle, pancreatic acinar calls, endothelial cells, astrocytes and lung. For example, promoters B29 r in B cells, CD14 in monocytic cells, CD43 in leukocytes and platelets, CD45 in haematopoietic cells, CD68 in macrophages, Desmin in muscle, Elastase-1r in pancreatic acinar cells, Endoglin in endothelial cells, Fibronectin in differentiating and healing tissue, Flt-1 in endothelial cells, GFAP in astrocytes, GPIIb in megakaryocytes, ICAM-2 in endothelial cells, INF-β and WASP in hematopoietic cells, Mb in muscle, Nphsl in podocytes, OG-2 in osteoblasts and odonblasts, SP-B in lung, SYN1 in neurons. In one example, a muscle cell specific expression control element, such that expression of an encoded product is restricted to the muscle cells in an individual, or to muscle cells in a mixed population of cells in culture, for example, an organ culture. Muscle cell specific expression control elements including, for example, the muscle creatine kinase promoter (Sternberg et al., Mol. Cell. Biol. 8:2896-2909, 1988) and the myosin light chain enhancer/promoter (Donoghue et al., Proc. Natl. Acad. Sci., USA 88:5847-5851, 1991) are well known in the art. Other tissue specific promoters, as well as expression control elements only expressed during particular developmental stages of a cell or organism are well known in the art.

In certain embodiments, a vector further comprises woodchuck hepatitis post-transcriptional regulatory element (WPRE), human hepatitis post-transcriptional regulatory element (HPRE) or a scaffold attachment region (SAR).

In certain embodiments, a vector further comprises a two or more transposon ends to facilitate integration of an expression cassette into the genome of an expression host. In certain embodiments, these integration-facilitating sequences include a TTAA-target or TTAT-target site specific insertion element. In certain embodiments the integration-facilitating sequences are recognized by an integrase or a transposase, in certain embodiments said integrase is a piggyBac integrase. In certain embodiments said vector further comprises a gene encoding said integrase. In certain embodiments, an expression vector further comprises Lentiviral LTR (long terminal repeats) to facilitate integration of an expression cassette into the genome of an expression host.

In certain embodiments, a vector further comprises a protein for genome modification, for example CRISPR or Cas9. Such a genome modifying vector further comprises promoters specific for RNA expression, for example, T5, T7, SP6, U6, H1 and more that work in a specific host to drive expression of RNA, for example guide RNA (gRNA). Such a vector can be used to drive expression of a single gRNA or multiple gRNAs can be incorporated by using the method for joining multiple polynucleotides described herein.

In some embodiments, the vector sizes can range from 1 kb to 20 kb or more. Since the vectors contain a toxic gene such as ccdB as described herein, there is no need for gel purification and therefore the vector is not limited in size.

In some embodiments, the insert fragments can range from 25 base pairs to 10 kb or more (for e.g. 25 or 30 or 40 or 50 or 60 or 70 or 80 or 1000 or 2000 or 3000 4000 or 5000 or 6000 or 7000 or 8000 or 9000 or 10000 or 11000 or 12000 or 13000 or 14000 or more base pairs, or any combination thereof). The use of typeIIs recognition sequences as described herein allow non-compatible overhangs to be generated at each end of the insert fragment thereby preventing the insert fragment from looping back on itself and self-ligating. This allows for a range of insert sizes without the possibility for self-ligation. Very large insert fragment sizes are also possible since the typeIIs restriction enzyme SapI as described herein has a 7 base pair recognition sequence that occurs at an average frequency of 1 in 8192 base pairs, which means that the likelihood of the site occurring within the insert sequence is very low. Since the method described herein allows for easy assembly of insert fragments from insert polynucleotides to a vector, the insert fragment needs to be cloned only once, therefore avoiding mutagenic events introduced by use of polymerases or recombinases, allowing for a greater range of insert fragment sizes.

Expression control and other elements useful in the vectors can be obtained in various ways. In particular, many of the elements are included in commercially available vectors and can be isolated there from and can be modified as disclosed herein. In addition, the sequences of or encoding the elements useful herein generally are well known and disclosed in publications. In many cases, the elements, for example, transcriptional and translational expression control elements, as well as compartmentalization domains, are relatively short sequences, and, therefore, are amenable to chemical synthesis of the element or a nucleotide sequence encoding the element.

A vector useful in the methods described herein also can encode a ribonucleic acid (RNA) molecule, which can function, for example, as a riboprobe, an antisense nucleic acid molecule, a ribozyme, or a triplexing nucleic acid molecule, or can be used in an in vitro translation reaction, and the second nucleic acid molecule can encode an expression control element useful for expressing an RNA from the first nucleic acid molecule. For example, where it is desired to produce a large amount of RNA, a second nucleic acid molecule component for performing a method as described herein can comprise an RNA polymerase promoter such as T7, T5, T3 or SP6 RNA polymerase promoter. Where the RNA molecule is to be expressed in a cell, for example, an antisense molecule to be expressed in a mammalian cell, the second (or other) nucleic acid molecule can include a promoter that is active in a mammalian cell, particularly a tissue specific promoter, which is active only in a target cell. Furthermore, where the RNA molecule is to be translated, for example, in a coupled in vitro transcription/translation reaction, the first nucleic acid molecule or second (or other) nucleic acid molecule can contain appropriate translational expression control elements.

In many of the embodiments described herein, the vectors can contain an origin of replication. However, it should be understood that the methods and compositions can work with vectors that do not comprise an origin of replication, e.g., vectors that integrate into the genome of a host following appropriate introduction into the host. Any such vector known to one skilled in the art without limitation can be used in the methods, compositions and kits.

Other embodiments include DNA and vectors useful in the methods of the present disclosure. In particular, polynucleotide molecules are provided, wherein one polynucleotide embodiment comprises a first DNA segment and a second DNA segment, the first or second segment comprising a selectable marker. A second polynucleotide embodiment comprises a first DNA segment and a second DNA segment, the first or second DNA segment comprising a toxic gene. A third Polynucleotide embodiment comprises a first DNA segment and a second DNA segment, the first or second DNA segment comprising an inactive fragment of at least one selectable marker, wherein the inactive fragment of the selectable marker is capable of reconstituting a functional selectable marker when combined into a product polynucleotide with another inactive fragment of at least one selectable marker derived from the vector.

7.1.7 Compatibility of Two or More Polynucleotides with Multiple Vectors

Sub-cloning of DNA segments is performed as a daily routine in many research labs. It is frequently performed in order to move a first polynucleotide sequence from a first vector into a second vector, where the second vector performs a function that is not performed by the first. Differences between the two vectors may include differences in selectable markers or differences in replicative sequences. They may also include differences in vector sequence elements that may directly interact with the first polynucleotide, for example by affecting expression of the first polynucleotide, or by encoding polypeptides that interact with or are joined to polypeptides encoded by the first polynucleotide.

When an insert polynucleotide and a vector are cleaved by their respective typeIIs restriction endonucleases, the resulting overhangs are not contained within the typeIIs recognition sequences so in principle any set of compatible overhangs may be selected. Thus it is possible to completely control the sequence of the product polynucleotide, without being forced to incorporate restriction sites or recombination sequences. This is an advantage of the present disclosure. In preferred embodiments an insert fragment derived from an insert polynucleotide may be ligated with a plurality of different vector fragments, all of which share the same pair of overhangs. This allows a plurality of sequence contexts to be explored in parallel. For example in embodiments where the insert fragment comprises a polynucleotide that encodes a polypeptide, it may be advantageous to express the encoded polypeptide under a plurality of conditions, for example under the control of one or more promoter, with one or more C-terminal fusion or one or more N-terminal fusion; under control of one or more ribosome binding sites; with one or more IRES or 2A peptide elements for bicistronic expression; under control of one or more transcription control elements that are host specific to determine conditions that yield the most preferred levels of expression, or the most preferred polypeptide solubility, or the most preferred polypeptide activity.

In preferred embodiments therefore, groups of vectors are designed so that the overhangs of a single insert fragment are compatible with the ends of any vector fragment selected from the group. In preferred embodiments the overhang comprises a sequence that can perform a specific function, in some embodiments the overhang comprises the sequence of a codon and in some embodiments the codon encodes a methionine or a glycine or a stop codon. In some embodiments an overhang comprises the sequence 5'-ATG-3', or 5'-CAT-3', or 5'-GGT-3', or 5'-ACC-3', or 5'-TAA-3', or 5'-TTA-3', or 5'-AATG-3', or 5'-CATT-3' or 5'-TAAA-3', or 5'-ATTT-3', or 5'-CCCC-3', or 5'-GGGG-3', or 5'-TTTT-3', or 5'-AAAA-3'.

Preferred embodiments comprise a plurality of vectors that are all useable with any open reading frame. Open reading frames all begin with a methionine codon (which is 5'-ATG-3') and end with a stop codon (5'-TAG-3', or 5'-TAA-3', or 5'-TGA-3'). Thus one preferred embodiment comprises a plurality of vectors that can be cut to produce vector fragments that are compatible with any insert fragment that has an overhang comprising 5'-ATG-3' at one end, and 5'-TAG-3', or 5'-TAA-3', or 5'-TGA-3' at the other end. Another preferred embodiment comprises a plurality of vectors that can be cut to produce vector fragments that have overhangs comprising 5'-ATG-3' at one end, and 5'-GGN-3', or 5'-GCN-3' at the other end and are ligatable with any insert fragment that has compatible overhangs. In some embodiments, a plurality of vectors that can be cut to produce vector fragments that have overhangs comprising 5'-AATG-3' at one end and 5'-CATT-3' or 5'-TAAA-3', or 5'-ATTT-3', or 5'-CCCC-3', or 5'-GGGG-3', or 5'-TTTT-3', or 5'-AAAA-3' at the other end and are ligatable with any insert fragment that has compatible overhangs.

The vector fragments comprise a transcriptional promoter which becomes operably linked to the ORF encoded in the insert genetic element fragments and insert fragment linking the two insert genetic elements when the multiple molecules are joined in a single reaction to form a product polynucleotide. The product polynucleotide is transformed into an expression host, where transcription from the promoter causes one of the ORFs encoded on the insert fragment to be expressed along with the second ORF that is linked to the first ORF by the insert polynucleotide comprising expression control or coupling elements. In a preferred embodiment the plurality of vectors differ from one another in sequences that control or influence expression, for example a promoter, a terminator, a ribosome biding site, a sequence that affects the initiation of translation, an enhancer, an element that affects the copy number of the vector in the expression host, an element that affects the site of genomic integration in an expression host. Thus two or more ORFs encoded in insert polynucleotides may be easily joined with a plurality of different vector fragments to obtain a construct producing desired expression properties. In some embodiments polynucleotides are joined with each of a plurality of vector fragments in a plurality of one pot reactions, each comprising two or more polynucleotides and a single vector fragment. In some embodiments two or more polynucleotides are joined with each of a plurality of vector fragments in a single reaction comprising two or more polynucleotides and a plurality of vector fragments. In some embodiments, a plurality of polynucleotides are each joined with a respective vector fragment in a plurality of vector fragments in a one pot reaction comprising a plurality of polynucleotides and a plurality of vector fragments.

In other preferred embodiments, a plurality of vector fragments comprise a transcriptional promoter and a sequence encoding a fusion tag, which is a polypeptide that confers a property affecting solubility, stability, proper folding, improved yields, localization, color or fluorescence of a protein, or affinity of a protein for a substrate, or a characteristic that facilitates purification or tracking of a protein in a cell. When insert fragments encoding two or more ORFs are joined with such a vector fragment in the one pot reaction to form a product polynucleotide, the product polynucleotide comprises a sequence encoding the fusion tag joined to an ORF encoded in one of the insert fragments.

In a preferred embodiment the plurality of vectors differ from one another in sequences that control or influence expression, or in the sequence and properties of the encoded fusion tag (which may be added to the C-terminus or the N-terminus of the polypeptide encoded in the insert fragment. Thus one ORF encoded in a polynucleotide may be easily joined with a plurality of different vector fragments to obtain a construct producing a polypeptide fusion with desired properties. In some embodiments two or more polynucleotides are joined with each of a plurality of vector fragments in a plurality of one pot reactions, each comprising a plurality of polynucleotides and a single vector fragment. In some embodiments two or more polynucleotides are joined with each of a plurality of vector fragments in a one pot reaction comprising the same two or more insert polynucleotides and a plurality of vector fragments. In some embodiments, a plurality of insert polynucleotides are each joined with a respective vector fragment in a plurality of vector fragments in a single reaction comprising a plurality of insert polynucleotides and a plurality of vector fragments.

When a product polynucleotide comprises a sequence encoding a polypeptide that originates in part from a vector fragment and in part from an insert fragment, if the vector fragment contributes the C-terminus of the encoded polypeptide, then the sequence from the insert fragment cannot end with a stop codon, as that would prevent a C-terminal fusion from the vector fragment. In this case it is advantageous instead to have open reading frames end with a codon that encodes an amino acid that is least likely to disrupt structure, and most likely to participate in a productive join to the C-terminally fused peptide or polypeptide. In preferred embodiments the open reading frame encoded in an insert fragment or an insert polynucleotide ends with a glycine codon or an alanine codon. In some embodiments the polynucleotide is cleaved in a one pot reaction to produce an overhang comprising 5'-ACC-3', or 5'-TCC-3', or 5'-GCC-3', or 5'-CCC-3', or 5'-TGC-3', or 5'-AGC-3', or 5'-CGC-3', or 5'-GGC-3' that is compatible with one end of a vector fragment. In some embodiments, the polynucleotide is cleaved in a one pot reaction to produce an overhang comprising 5'-CATT-3' or 5'-TAAA-3', or 5'-ATTT-3', or 5'-CCCC-3', or 5'-GGGG-3', or 5'-TTTT-3', or 5'-AAAA-3' that is compatible with one end of a vector fragment.

In a most preferred embodiment, two or more insert fragments comprising sequences that encode polypeptides can be subcloned into a plurality of vector fragments, wherein the vector fragments may differ from one another in sequences that control or influence expression, or they may differ from one another in sequences that encode a fusion tag, or both. Such a system has the advantage that the two or more polynucleotides need be prepared and sequenced only once, and then can be transferred simply and easily with the fidelity of restriction digestion and ligation (which is less mutagenic than assembly techniques that require in vitro DNA polymerases), but without the residual sequence element "scars" that result from recombinase action. An example of such a preferred embodiment is a plurality of vectors which can be cleaved by a typeIIs enzyme to produce an overhang comprising 5'-CAT-3' at one end at one end and either 5'-GGT-3', or 5'-GGA-3', or 5'-GGC-3', or 5'-GGG-3', or 5'-GCT-3', or 5'-GCA-3', or 5'-GCC-3', or 5'-GCG-3' at the other end or 5'-AATG-3' at one end and 5'-CATT-3' or 5'-TAAA-3', or 5'-ATTT-3', or 5'-CCCC-3', or 5'-GGGG-3', or 5'-TTTT-3', or 5'-AAAA-3' at the other end. In preferred embodiments each vector fragment in the plurality of vector fragments has the same two overhangs.

As described herein, the specialized vectors used for subcloning DNA segments are functionally diverse. These include but are not limited to: vectors for expressing genes in various organisms; for regulating gene expression; for providing tags to modify polypeptide properties such as solubility, localization, affinity for a substrate, color, fluorescence, characteristics that facilitate protein purification and characteristics that facilitate tracking of proteins in cells; for modifying the cloned DNA segment (e.g., generating deletions); for the synthesis of probes (e.g., riboprobes); for the preparation of templates for DNA sequencing; for the identification of protein coding regions; for the fusion of various protein-coding regions; for expressing one or more enzymes to catalyze a reaction and for providing large amounts of the DNA of interest. It is common that a particular investigation will involve subcloning the DNA segment(s) of interest into several different specialized vectors. By designing specialized acceptor vectors with appropriate typeIIs restriction sites flanking the cloning site, any nucleotide fragment encoding an open reading frame of interest can be quickly and efficiently cloned into one or multiple expression vectors. The nucleotide fragment can either be cloned into an insert polynucleotide as described herein or can be amplified with flanking typeIIs recognition sequences using PCR. PCR products can be directly cloned into any of the specialized vectors.

7.1.8 Kits for One Step Cloning Using TypeIIs Restriction Endonucleases

Further provided are kits for one-step typeIIs cloning. In certain embodiments, the kit comprises a vector that will support one step type IIs cloning, typeIIs restriction enzymes and T4 DNA ligase mix. In certain embodiments, the kits comprise one or more reagents (e.g., 1, or 2, or 3, or 4, or 5, or 6, or 7, or 8, or 9, or 10, or 11, or 12, or 13, or 14, or 15, or more) useful for performing a method as described herein. In one embodiment, the kit comprises a nucleic acid, e.g., a vector, suitable for use in a method described herein. Two or more typeIIs restriction endonucleases can also be part of the kit. The nucleic acid in the kit can, but need not be a vector and can contain one or more (e.g., 1, or 2, or 3, or 4, or 5, or 6, or 7, or 8, or 9, or 10, or 11, or 12, or 13, or 14, or 15, or more) expression control elements. In certain embodiments, the kit comprises instructions for using kit components.

A kit can include a plurality of nucleic acid molecules, wherein each nucleic acid molecule in the plurality has a first end and a second end, wherein the first end includes a 5' nucleotide sequence that is complementary to a 5' overhang of the first nucleic acid molecule, e.g., the vector and wherein the second end of the last nucleic acid molecule includes a 3' nucleotide sequence that is complementary to a 3' overhang of the first nucleic acid molecule, e.g., the vector. The two or more nucleic acid molecules in the plurality can encode a plurality of transcriptional regulatory elements, translational regulatory elements, or a combination thereof, or can encode a plurality of peptides, such as peptide tags, cell compartmentalization domains and protease cleavage sites.

In one embodiment, a kit comprises a) an enzyme mixture comprising the first and second typeIIs restriction endonucleases that recognize a first typeIIs recognition sequence and a second typeIIs recognition sequence and a DNA ligase, b) a reaction buffer, and c) instructions for incubating the enzyme mixture, the reaction buffer, and the first polynucleotide, the insert polynucleotide and other polynucleotides comprising genetic elements for a predetermined length of time, and transforming the mixture into a host cell. In some embodiments, the two typeIIs restriction enzymes are BsaI and SapI. In a specific embodiment, the kit further comprises the first and second polynucleotides. In some embodiments, the first polynucleotide is a vector. The vector may be provided as a linear polynucleotide or a circular plasmid. The second polynucleotide may be a linear polynucleotide or a circular plasmid and comprises expression control elements or coupling elements as described above to drive expression of the insert genetic elements.

A nucleic acid molecule component of a kit can be, for example, a circularized or linearized vector such as a cloning vector or expression vector. If desired, such a kit can contain a plurality of nucleic acid molecules, each comprising a different expression control element or other element such as, but not limited to a sequence encoding tag or other detectable molecule or a cell compartmentalization domain. The different elements can be different types of a particular expression control element, for example, constitutive or inducible promoters or tissue specific promoters, or can be different types of elements including, for example, transcriptional and translational expression control elements and epitope tags. In addition, the plurality of nucleic acid molecules can have 5' overhanging sequences that are unique to a particular expression control element, or that are common to a plurality of related expression control elements, for example, to a plurality of different promoter elements. The 5' overhanging sequences of nucleic acid molecules can be designed such that one or more expression control elements contained on the nucleic acid molecule can be operatively directionally linked to provide a useful function, for example, an element comprising a Kozak sequence and an element comprising a translation start site can have complementary 5' overhangs such that the elements can be operatively linked as described herein.

Further provided are kits for linking nucleic acid molecules using methods described herein. Thus, kits may comprise one or more components for performing methods described herein. In particular embodiments, the kits may comprise one or more components selected from the group consisting of instructions for use of kits components, one or more buffers, one or more nucleic acid molecules (e.g., one or more nucleic acid molecules having a 5' overhang or a 3' overhang or a 5' overhang and a 3' overhang or two 5' overhangs or two 3' overhangs or more.), one or more typeIIs endonucleases, one or more ligase, one or more adapter linker for preparing molecules having a 5' overhang and/or a 3' overhang, and/or one or more containers in which to perform methods described herein. In certain embodiments, the kits comprise a buffer in which both a typeIIs restriction endonuclease and a DNA ligase are active.

8. EXAMPLES

The following examples are intended to illustrate the methods, compositions and kits disclosed herein and should not be construed as limiting in any way. Various equivalents will be apparent to one skilled in the art from the following examples; such equivalents are also contemplated to be part of the disclosure disclosed herein.

8.1 Multi-Part Assembly

We have developed a method for joining three or more polynucleotides in a single reaction with high efficiency. The method uses two different type IIs restriction enzymes that generate different length overhangs such that the polynucleotides are joined together in a directional manner in the presence of DNA ligase to form the product polynucleotide. In preferred embodiments, the overhangs generated by the typeIIs restriction enzymes are 4 bases and 3 bases in length. In some preferred embodiments, the typeIIs restriction enzymes are BsaI and SapI.

Assembly of light chain and heavy chain of antibody Herceptin coupled by an IRES element or with a second promoter and a vector fragment to generate a single construct or product polynucleotide that expresses the two ORFs, one expressing the light chain and the other a heavy chain of antibody Herceptin in a single reaction is described. We used polynucleotides one encoding light chain (LC) 223757 (SEQ ID NO:1) in pM269 (DNA2.0) with flanking BsaI and SapI recognition sites, an insert polynucleotide encoding coupling element IRES 186571 (SEQ ID NO: 3) in pM269 or regulatory elements comprising an enhancer CMV, GAPDH promoter and CMVc intron 223883 (SEQ ID NO: 4) in pM269 with flanking SapI sites, another polynucleotide encoding heavy chain (HC) 223758 (SEQ ID NO: 2) with flanking SapI and BsaI sites and a vector fragment pD2539 (DNA2.0) with 4 base overhangs generated by BsaI.

Seven reactions were set up in parallel, reaction 5, Table 1 with insert polynucleotide comprising IRES and reaction 6, Table 1 with insert polynucleotide comprising regulatory elements described above: each reaction was set up in a 10 µl reaction with 50 mM potassium acetate, 20 mM Tris-acetate, 10 mM magnesium acetate, 1 mM dithiothreitol, pH7.9, 1 mM ATP, 50 ng of polynucleotide 223757 (SEQ ID NO: 1), 50 ng of polynucleotide 223758 (SEQ ID NO: 2), 50 ng of insert polynucleotide, either 186571 (SEQ ID NO: 3) or 223883 (SEQ ID NO: 4) and 50 ng of vector fragment pD2539 (DNA2.0), an enzyme mix consisting of 2.5 units BsaI, 2.5 units of SapI and 100 units T4 DNA ligase. Buffer, ATP and enzymes were from New England Biolabs. Reactions 1 and 2 and 3 and 4 lacked one of the polynucleotides and reaction 7 contained all the components except enzyme. Incubation was carried out at 37° C. for 60 minutes. 2.5 µl of each reaction was transformed into NEB 10-Beta cells, 1 ml SOC added and grown for 1 hour at 37° C. 10 µl of cultures were plated on LB Agar+30 µg/ml kanamycin. Results are shown in Table 1.

TABLE 1

| Reaction | 223757 (SEQ ID NO: 1) | 223758 (SEQ ID NO: 2) | 186571 (SEQ ID NO: 3) | 223883 (SEQ ID NO: 4) | CFU/10 µl |
| --- | --- | --- | --- | --- | --- |
| 1 | 50 ng | 0 | 0 | 0 | 0 |
| 2 | 0 | 50 ng | 0 | 0 | 0 |
| 3 | 0 | 0 | 50 ng | 0 | 0 |
| 4 | 0 | 0 | 0 | 50 ng | 0 |
| 5 | 50 ng | 50 ng | 50 ng | 0 | 40 |
| 6 | 50 ng | 50 ng | 0 | 50 ng | 40 |
| 7 (no enzyme control) | 50 ng | 50 ng | 50 ng | 50 ng | 0 |

We observed 100% of the colonies picked (reactions 5 and 6, Table 1) comprised all polynucleotides assembled in the expected configuration indicating that the single reaction assembly of the multiple polynucleotides with different length overhangs was very efficient. In contrast, assembly of the three or more polynucleotides with the same length overhang generated by a single typeIIs restriction enzyme, for example either BsaI or SapI alone gave only 80-90% of transformants with the correct configuration (data not shown). Product polynucleotides were transformed and tested for antibody expression in Chinese Hamster ovary (CHO) cells showing good expression (data not shown). Sequencing and expression results combined showed that the assembly of polynucleotides was scarless with no additional scar sequences interfering with expression.

SEQUENCES

SEQ ID NO: 1_223757_LC
```
CGCTGAAGGTCTCTGGGGAGCTTGCTTGTTCTTTTTGCAGAAGCTCAGAA
TAAACGCTCAACTTTGGCCGCCACCATGGAGTGGACATGGGTCTTTCTGT
TCCTTCTTTCCGTCACCGCTGGAGTGCATAGCGACATCCAGATGACCCAG
TCTCCATCCTCCCTGTCTGCATCTGTAGGAGACAGAGTCACCATCACTTG
CCGGGCAAGTCAGGACGTCAATACCGCCGTCGCCTGGTATCAGCAGAAAC
CAGGGAAAGCCCCTAAGCTCCTGATCTATTCCGCCTCCTTCCTCTATAGT
GGGGTCCCATCAAGGTTCAGTGGCAGTCGGTCTGGGACAGATTTCACTCT
CACCATCAGCAGTCTGCAACCTGAAGATTTTGCAACTTACTACTGTCAAC
AGCATTACACCACCCCTCCAACCTTCGGCCAAGGGACCAAGGTGGAAATC
AAACGAACTGTGGCTGCACCATCTGTCTTCATCTTCCCGCCATCTGATGA
GCAGTTGAAATCTGGAACTGCCTCTGTTGTGTGCCTGCTGAATAACTTCT
ATCCCAGAGAGGCCAAAGTACAGTGGAAGGTGGATAACGCCCTCCAATCG
GGTAACTCCCAGGAGAGTGTCACAGAGCAGGACAGCAAGGACAGCACCTA
CAGCCTCAGCAGCACCCTGACGCTGAGCAAAGCAGACTACGAGAAACACA
AAGTCTACGCCTGCGAAGTCACCCATCAGGGCCTGAGCTCGCCCGTCACA
AAGAGCTTCAACAGGGGAGAGTGTTAAGGTAGAAGAGCCGTCAAAAGGGC
GACACAAAATT
```

SEQ ID NO: 2_223758_HC
```
CGCTGAAGCTCTTCTATGGAGTTGGGGCTGTGCTGGGTTTTCCTTGTTGC
TATTTTAGAAGGTGTCCAGTGTGAGGTGCAGCTGGTGGAGTCTGGGGGAG
GCTTGGTCCAGCCTGGGGGGTCCCTGAGACTCTCCTGTGCAGCCTCTGGA
TTCAACATCAAGGACACCTACATTCATTGGGTCCGCCAGGCTCCAGGGAA
GGGGCTGGAGTGGGTCGCCAGAATCTACCCAACGAACGGGTACACAAGAT
ACGCAGACTCCGTGAAGGGCAGATTCACCATCTCCGCTGACACGTCCAAG
AACACGGCCTATCTTCAAATGAACAGCCTGAGAGCCGAGGACACGGCTGT
GTATTACTGTTCCAGATGGGGGGGCGACGGCTTCTACGCTATGGACTACT
GGGGCCAAGGAACCCTGGTCACCGTCTCCTCAGCCTCCACCAAGGGCCCA
TCGGTCTTCCCCCTGGCACCCTCCTCCAAGAGCACCTCTGGGGGCACAGC
GGCCCTGGGCTGCCTGGTCAAGGACTACTTCCCCGAACCGGTGACGGTGT
CGTGGAACTCAGGCGCCCTGACCAGCGGCGTGCACACCTTCCCGGCTGTC
CTACAGTCCTCAGGACTCTACTCCCTCAGCAGCGTGGTGACCGTGCCCTC
CAGCAGCTTGGGCACCCAGACCTACATCTGCAACGTGAATCACAAGCCCA
GCAACACCAAGGTGGACAAGAAAGTTGAGCCCAAATCTTGTGACAAAACT
CACACATGCCCACCGTGCCCAGCACCTGAACTCCTGGGGGGACCGTCAGT
CTTCCTCTTCCCCCCAAAACCCAAGGACACCCTCATGATCTCCCGGACCC
CTGAGGTCACATGCGTGGTGGTGGACGTGAGCCACGAAGACCCTGAGGTC
AAGTTCAACTGGTACGTGGACGGCGTGGAGGTGCATAATGCCAAGACAAA
GCCGCGGGAGGAGCAGTACAACAGCACGTACCGGGTGGTCAGCGTCCTCA
CCGTCCTGCACCAGGACTGGCTGAATGGCAAGGAGTACAAGTGCAAGGTG
TCCAACAAAGCCCTCCCAGCCCCCATCGAGAAAACCATCTCCAAAGCCAA
AGGGCAGCCCCGAGAACCACAGGTGTACACCCTGCCCCCATCCCGGGATG
AGCTGACCAAGAACCAGGTCAGCCTGACCTGCCTGGTCAAAGGCTTCTAT
CCCAGCGACATCGCCGTGGAGTGGGAGAGCAATGGGCAGCCGGAGAACAA
CTACAAGACCACGCCTCCCGTGCTGGACTCCGACGGCTCCTTCTTCCTCT
ACAGCAAGCTCACCGTGGACAAGAGCAGGTGGCAGCAGGGGAACGTCTTC
TCATGCTCCGTGATGCATGAGGCTCTGCACAACCACTACACGCAAAAGAG
CCTCTCCCTGTCTCCGGGTAAATAAAAAAAGAGACCCGTCAAAAGGGCGA
CACAAAATT
```

SEQ ID NO: 3_IR_186571
```
CCCCCCCCCTAACGTTACTGGCCGAAGCCGCTTGGAATAAGGCCGGTGTG
CGTTTGTCTATATGTTATTTTCCACCATATTGCCGTCTTTTGGCAATGTG
AGGGCCCGGAAACCTGGCCCTGTCTTCTTGACGAGCATTCCTAGGGGTCT
TTCCCCTCTCGCCAAAGGAATGCAAGGTCTGTTGAATGTCGTGAAGGAAG
CAGTTCCTCTGGAAGCTTCTTGAAGACAAACAACGTCTGTAGCGACCCTT
TGCAGGCAGCGGAACCCCCCACCTGGCGACAGGTGCCTCTGCGGCCAAAA
GCCACGTGTATAAGATACACCTGCAAAGGCGGCACAACCCCAGTGCCACG
TTGTGAGTTGGATAGTTGTGGAAAGAGTCAAATGGCTCTCCTCAAGCGTA
TTCAACAAGGGGCTGAAGGATGCCCAGAAGGTACCCCATTGTATGGGATC
TGATCTGGGGCCTCGGTACACATGCTTTACATGTGTTTAGTCGAGGTTAA
AAAACGTCTAGGCCCCCCGAACCACGGGGACGTGGTTTTCCTTTGAAAAA
CACGATGATAATATGGCCACAACC
```

SEQ ID NO: 4_DP_223883
```
GGTATCGGGGAGGCTAACTGAAACACGGAAGGAGACAATACCGGAAGGA
ACCCGCGCTATGACGGCAATAAAAAGACAGAATAAAACGCACGGGTGTTG
GGTCGTTTGTTCATAAACGCGGGGTTCGGTCCCAGGGCTGGCACTCTGTC
GATACCCCACCGAGTCCCCATTGGGGCCAATACGCCCGCGTTTCTTCCTT
TTCCCCACCCCACCCCCCAAGTTCGGGTGAAGGCCCAGGGCTCGCAGCCA
ACGTCGGGGCGGCAGGCCCTGCCATAGAAATCGATAATATATGGTAGGGT
TCATAGCCAGAGTAACCTTTTTTTTTAATTTTTATTTTATTTTATTTTTG
AGTCGGGCGCGCCAAAATGAAGTGAAGTTCCTATACTTTCTAGAGCGAGC
TCACGGGACAGCCCCCCCCAAAGCCCCCAGGGATGTAATTACGTCCCT
CCCCCGCTAGGGGGCAGCAGCGAGCCGCCCGGGGCTCCGCTCCGGTCCGG
CGCTCCCCCCGCATCCCCGAGCCGGCAGCGTGCGGGACAGCCCGGGCAC
GGGGAAGGTGGCACGGGATCGCTTTCCTCTGAACGCTTCTCGCTGCTCTT
TGAGCCTGCAGACACCTGGGGGGATACGGGGAAAAAGCTTTAGGCTGAAA
GAGAGATTTAGAATGACAGGCGAGCTCACGGGGACAGCCCCCCCCCAAAG
```

```
CCCCCAGGGATGTAATTACGTCCCTCCCCCGCTAGGGGCAGCAGCGAGC
CGCCCGGGGCTCCGCTCCGGTCCGGCGCTCCCCCCGCATCCCCGAGCCGG
CAGCGTGCGGGGACAGCCCGGGCACGGGGAAGGTGGCACGGGATCGCTTT
CCTCTGAACGCTTCTCGCTGCTCTTTGAGCCTGCAGACACCTGGGGGAT
ACGGGGAAAAAGCTTGAAACTTGATCTGTCGCCGCAATTCAAGCTTCGTG
AGGCTCCGGTGCCCGTCAGTGACCTGCTATACTCTGGAGACGACTTACGG
TAAATGGCCCGCCTGGCTGACCGCCCAACGACCCCCGCCCATTGACGTCA
ATAATGACGTATGTTCCCATAGTAACGCCAATAGGGACTTTCCATTGACG
TCAATGGGTGGAGTATTTACGGTAAACTGCCCACTTGGCAGTACATCAAG
TGTATCATATGCCAAGTCCGCCCCCTATTGACGTCAATGACGGTAAATGG
CCCGCCTGGCATTATGCCCAGTACATGACCTTACGGGACTTTCCTACTTG
GCAGTACATCTACGTATTAGTCATCGCTATTACCAATGACGTCGAGGAGA
AGTTCCCCAACTTTCCCGCCTCTCAGCCTTTGAAAGAAAGAAAGGGGAGG
GGGCAGGCCGCGTGCAGCCGCGAGCGGTGCTGGGCTCCGGCTCCAATTCC
CCATCTCAGTCGTTCCCAAAGTCCTCCTGTTTCATCCAAGCGTGTAAGGG
TCCCCGTCCTTGACTCCCTAGTGTCCTGCTGCCCACAGTCCAGTCCTGGG
AACCAGCACCGATCACCTCCCATCGGGCCAATCTCAGTCCCTTCCCCCCT
ACGTCGGGGCCCACACGCTCGGTGCGTGCCCAGTTGAACCAGGCGGCTGC
GGAAAAAAAAAGCGGGGAGAAAGTAGGGCCCGGCTACTAGCGGTTTTAC
GGGCGCACGTAGCTCAGGCCTCAAGACCTTGGGCTGGGACTGGCTGAGCC
TGGCGGGAGGCGGGGTCCGAGTCACCGCCTGCCGCCGCGCCCCCGGTTTC
TATAAATTGAGCCCGCAGCCTCCCGCTTCGCTCTCTGCTCCTCCTGTTCG
ACAGTCAGCCGCATCTTCTTTTGCGTCGCCAGCGTCTCAGGGGCCCTGGC
AGAACTCGGTAAGTCTGTTGACATGTATGTGATGTATACTAACCTGCATG
GGACGTGGATTTACTTGTGTATGTCAGATAGAGTAAAGATTAACTCTTGC
ATGTGAGCGGGGCATCGAGATAGCGATAAATGAGTCAGGAGGACGGATAC
TTATATGTGTTGTTATCCTCCTCTACAGTCAAACAGATTAAGGGGTAGCT
TGCTTGTTCTTTTTGCAGAAGCTCAGAATAAACGCTCAACTTTGGCCGCC
ACCATG
```

9. REFERENCES

All references cited herein are incorporated herein by reference in their entirety and for all purposes to the same extent as if each individual publication or patent or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

---

What is claimed is:

1. A method of forming a product polynucleotide comprising:
forming a reaction mixture comprising (i) a vector fragment whose ends have four base overhangs resulting from cleavage of a vector with a first type IIs enzyme, (ii) a first insert nucleic acid with a four base overhang at one end resulting from cleavage by the first type IIs enzyme and a three base overhang at the other end resulting from cleavage by a second type IIs enzyme; and (iii) a second insert nucleic acid with a four base overhang at one end resulting from cleavage by the first type IIs enzyme and a three base overhang at the other end resulting from cleavage by the second type IIs enzyme, and (iv) a ligase, wherein the four base overhangs of the vector ligate with the four base overhangs of the first and second inserts and the three base overhangs of the first and second inserts ligate with each other or three base overhangs of a spacer nucleic acid resulting from cleavage with the second type IIs enzyme to form a product polynucleotide in which the first and second insert nucleic acids are joined to the vector fragment by a single reaction of joining multiple polynucleotides.

2. The method of claim 1, further comprising the spacer nucleic acid with three base overhangs at each end resulting from cleavage with the second type IIs enzyme such that the three base overhangs of the spacer nucleic acid ligate with the three base overhangs of the first and second insert nucleic acids to form a product polynucleotide in which the spacer nucleic acid flanked by a first and second insert nucleic acids is joined to the vector fragment.

3. The method of claim 1 wherein the first type IIs enzyme is BsaI and the second type IIs enzyme is SapI.

4. The method of claim 1, wherein the first and second insert nucleic acids each encodes a polypeptide.

5. The method of claim 1, wherein the first and second insert nucleic acids encode antibody heavy and light chains.

6. The method of claim 2, wherein the spacer nucleic acid comprises a promoter, placed in operable linkage with the second insert nucleic acid in the product polynucleotide.

7. The method of claim 2, wherein the spacer nucleic acid comprises an internal ribosome entry site (IRES), placed in operable linkage with the second insert nucleic acid in the product polynucleotide.

8. The method of claim 1, wherein the vector fragment comprises a promoter, placed in operable linkage with the first insert nucleic acid in the product polynucleotide.

9. The method of claim 1, wherein each of the vector fragment, first and second insert nucleic acid and spacer nucleic acid lack recognition sites for the type IIs enzyme that generated its overhang ends.

10. The method of claim 1, wherein overhangs are generated by cleavage by the first and second type IIs enzymes in the reaction mixture.

11. The method of claim 10, wherein the vector fragment is generated in the reaction mixture by cleavage of a vector comprising a counter-selectable marker or by cleavage of a linear vector.

12. The method of claim 11, wherein the counter-selectable marker is selected from a group consisting of sacB, rpsL, tetAR, pheS, thyA, lacY, gata-1, ccdB, kid and barnase.

13. The method of claim 1, wherein overhangs are generated before forming the reaction mixture.

14. The method of claim 1 further comprising transforming the mixture into a host cell, and growing the host cell under conditions that select for the presence of a selectable marker encoded by the vector fragment or spacer nucleic acid and, optionally, isolating the product polynucleotide from the host cell.

15. The method of claim 4, wherein the product polynucleotide encodes a fusion protein comprising the polypeptides encoded by the first and second insert nucleic acid.

16. The method of claim 4, wherein ligation of the three base overhang of the first insert nucleic acid and the three base overhang of the spacer generates a stop codon for the polypeptide encoded by the first insert nucleic acid.

17. The method of claim 4, wherein ligation of the three base overhang of the second insert nucleic acid and three base overhang of the spacer generates an initiation codon for the polypeptide encoded by the second insert nucleic acid.

18. The method of claim 1, wherein ligation of the three base overhang of the first insert nucleic acid and the three base overhang of the second insert nucleic acid forms a glycine or alanine codon expressed as a glycine or alanine between the first and second polypeptides in a fusion protein.

19. The method of claim 2, wherein the spacer encodes a peptide and ligation of the three base overhang of the first insert nucleic acid and a three base overhang of the spacer forms a glycine or alanine codon expressed as a glycine or alanine between the first polypeptide and the peptide encoded by the spacer.

20. The method of claim 2, wherein the spacer encodes a peptide and ligation of the three base overhang of the second insert nucleic acid and a three base overhang of the spacer forms a glycine or alanine codon expressed as a glycine or alanine between second polypeptide and the peptide encoded by the spacer.

* * * * *

SEQUENCE LISTING

```
<160> NUMBER OF SEQ ID NOS: 4

<210> SEQ ID NO 1
<211> LENGTH: 811
<212> TYPE: DNA
<213> ORGANISM: Homo sapiens

<400> SEQUENCE: 1
cgctgaaggt ctctggggag cttgcttgtt cttttgcag aagctcagaa taaacgctca         60
actttggccg ccaccatgga gtggacatgg gtctttctgt tccttctttc cgtcaccgct        120
ggagtgcata gcgacatcca gatgacccag tctccatcct ccctgtctgc atctgtagga       180
gacagagtca ccatcacttg ccgggcaagt caggacgtca ataccgccgt cgcctggtat       240
cagcagaaac cagggaaagc ccctaagctc ctgatctatt ccgcctcctt cctctatagt       300
ggggtcccat caaggttcag tggcagtcgg tctgggacag atttcactct caccatcagc       360
agtctgcaac tgaagatttt gcaacttac tactgtcaac agcattacac caccctcca         420 accttcggcc aagggaccaa ggtggaaatc aaacgaactg tggctgcacc atctgtcttc       480
atcttcccgc catctgatga gcagttgaaa tctggaactg cctctgttgt gtgcctgctg       540
aataacttct atcccagaga ggccaaagta cagtggaagg tggataacgc cctccaatcg       600
ggtaactccc aggagagtgt cacagagcag gacagcaagg acagcaccta cagcctcagc       660
agcaccctga cgctgagcaa agcagactac gagaaacaca aagtctacgc ctgcgaagtc       720
acccatcagg gcctgagctc gcccgtcaca aagagcttca cagggagga gtgttaaggt        780 agaagagccg tcaaaagggc gacacaaaat t                                       811
```

<210> SEQ ID NO 2
<211> LENGTH: 1459
<212> TYPE: DNA
<213> ORGANISM: Homo sapiens

<400> SEQUENCE: 2

| | | | | | |
|---|---|---|---|---|---|
| cgctgaagct | cttctatgga | gttggggctg | tgctgggttt | tccttgttgc | tattttagaa | 60 |
| ggtgtccagt | gtgaggtgca | gctggtggag | tctgggggag | gcttggtcca | gcctggggggg | 120 |
| tccctgagac | tctcctgtgc | agcctctgga | ttcaacatca | aggacaccta | cattcattgg | 180 |
| gtccgccagg | ctccagggaa | ggggctgag | tgggtcgcca | gaatctaccc | aacgaacggg | 240 |
| tacacaagat | acgcagactc | cgtgaagggc | agattcacca | tctccgctga | cacgtccaag | 300 |
| aacacggcct | atcttcaaat | gaacagcctg | agagccgagg | acacggctgt | gtattactgt | 360 |
| tccagatggg | ggggcgacgg | cttctacgct | atggactact | ggggccaagg | aaccctggtc | 420 |
| accgtctcct | cagcctccac | caagggccca | tcggtcttcc | ccctggcacc | ctcctccaag | 480 |
| agcacctctg | ggggcacagc | ggccctgggc | tgcctggtca | aggactactt | ccccgaaccg | 540 |
| gtgacggtgt | cgtggaactc | aggcgccctg | accagcggcg | tgcacacctt | cccggctgtc | 600 |
| ctacagtcct | caggactcta | ctccctcagc | agcgtggtga | ccgtgccctc | cagcagcttg | 660 |
| ggcacccaga | cctacatctg | caacgtgaat | cacaagccca | gcaacaccaa | ggtggacaag | 720 |
| aaagttgagc | ccaaatcttg | tgacaaaact | cacacatgcc | caccgtgccc | agcacctgaa | 780 |
| ctcctggggg | gaccgtcagt | cttcctcttc | cccccaaaac | ccaaggacac | cctcatgatc | 840 |
| tcccggaccc | ctgaggtcac | atgcgtggtg | gtggacgtga | gccacgaaga | ccctgaggtc | 900 |
| aagttcaact | ggtacgtgga | cggcgtggag | gtgcataatg | ccaagacaaa | gccgcgggag | 960 |
| gagcagtaca | acagcacgta | ccgggtggtc | agcgtcctca | ccgtcctgca | ccaggactgg | 1020 |
| ctgaatggca | aggagtacaa | gtgcaaggtg | tccaacaaag | ccctcccagc | ccccatcgag | 1080 |
| aaaaccatct | ccaaagccaa | agggcagccc | cgagaaccac | aggtgtacac | cctgcccccca | 1140 |
| tcccgggatg | agctgaccaa | gaaccaggtc | agcctgacct | gcctggtcaa | aggcttctat | 1200 |
| cccagcgaca | tcgccgtgga | gtgggagagc | aatgggcagc | cggagaacaa | ctacaagacc | 1260 |
| acgcctcccg | tgctggactc | cgacggctcc | ttcttcctct | acagcaagct | caccgtggac | 1320 |
| aagagcaggt | ggcagcaggg | gaacgtcttc | tcatgctccg | tgatgcatga | ggctctgcac | 1380 |
| aaccactaca | cgcaaaagag | cctctccctg | tctccgggta | aatgaaaaaa | gagacccgtc | 1440 |
| aaaagggcga | cacaaaatt | | | | | 1459 |

<210> SEQ ID NO 3
<211> LENGTH: 574
<212> TYPE: DNA
<213> ORGANISM: Encephalomyocarditis virus

<400> SEQUENCE: 3

| | | | | | |
|---|---|---|---|---|---|
| cccccccct | aacgttactg | gccgaagccg | cttggaataa | ggccggtgtg | cgtttgtcta | 60 |
| tatgttattt | tccaccatat | tgccgtcttt | tggcaatgtg | agggcccgga | aacctggccc | 120 |
| tgtcttcttg | acgagcattc | ctaggggtct | ttcccctctc | gccaaaggaa | tgcaaggtct | 180 |
| gttgaatgtc | gtgaaggaag | cagttcctct | ggaagcttct | tgaagacaaa | caacgtctgt | 240 |
| agcgaccctt | tgcaggcagc | ggaaccccccc | acctggcgac | aggtgcctct | gcggccaaaa | 300 |
| gccacgtgta | taagatacac | ctgcaaaggc | ggcacaaccc | cagtgccacg | ttgtgagttg | 360 |
| gatagttgtg | gaaagagtca | aatggctctc | ctcaagcgta | ttcaacaagg | ggctgaagga | 420 |

| | |
|---|---:|
| tgcccagaag gtacccatt gtatgggatc tgatctgggg cctcggtaca catgctttac | 480 |
| atgtgtttag tcgaggttaa aaaacgtcta ggccccccga accacgggga cgtggttttc | 540 |
| ctttgaaaaa cacgatgata atatggccac aacc | 574 |

<210> SEQ ID NO 4
<211> LENGTH: 2106
<212> TYPE: DNA
<213> ORGANISM: Homo sapiens

<400> SEQUENCE: 4

| | |
|---|---:|
| ggtatcgggg gaggctaact gaaacacgga aggagacaat accggaagga acccgcgcta | 60 |
| tgacggcaat aaaagacag aataaaacgc acgggtgttg ggtcgtttgt tcataaacgc | 120 |
| ggggttcggt cccagggctg gcactctgtc gataccccac cgagtcccca ttggggccaa | 180 |
| tacgcccgcg tttcttcctt tccccaccc cacccccaa gttcgggtga aggcccaggg | 240 |
| ctcgcagcca acgtcggggc ggcaggccct gccatagaaa tcgataatat atggtagggt | 300 |
| tcatagccag agtaaccttt tttttttaatt tttattttat tttattttg agtcgggcgc | 360 |
| gccaaaatga agtgaagttc ctatactttc tagagcgagc tcacggggac agccccccc | 420 |
| caaagccccc agggatgtaa ttacgtccct ccccgctag ggggcagcag cgagccgccc | 480 |
| ggggctccgc tccggtccgg cgctccccc gcatcccga gccggcagcg tgcgggaca | 540 |
| gcccgggcac ggggaaggtg gcacgggatc gctttcctct gaacgcttct cgctgctctt | 600 |
| tgagcctgca gacacctggg gggatacggg gaaaaagctt taggctgaaa gagagattta | 660 |
| gaatgacagg cgagctcacg gggacagccc ccccaaag ccccaggga tgtaattacg | 720 |
| tccctccccc gctaggggc agcagcgagc cgcccgggc tccgctccgg tccggcgctc | 780 |
| cccccgcatc cccgagccgg cagcgtgcgg ggacagcccg ggcacgggga aggtggcacg | 840 |
| ggatcgcttt cctctgaacg cttctcgctg ctctttgagc ctgcagacac ctgggggat | 900 |
| acggggaaaa agcttgaaac ttgatctgtc gccgcaattc aagcttcgtg aggctccggt | 960 |
| gcccgtcagt gacctgctat actctggaga cgacttacgg taaatggccc gcctggctga | 1020 |
| ccgcccaacg acccccgccc attgacgtca ataatgacgt atgttcccat agtaacgcca | 1080 |
| atagggactt ccattgacg tcaatggtg gagtatttac ggtaaactgc ccacttggca | 1140 |
| gtacatcaag tgtatcatat gccaagtccg cccctattg acgtcaatga cggtaaatgg | 1200 |
| cccgcctggc attatgccca gtacatgacc ttacgggact ttcctacttg gcagtacatc | 1260 |
| tacgtattag tcatcgctat taccaatgac gtcgaggaga agttccccaa ctttcccgcc | 1320 |
| tctcagcctt tgaaagaaag aaagggagg gggcaggccg cgtgcagccg cgagcggtgc | 1380 |
| tgggctccgg ctccaattcc ccatctcagt cgttcccaaa gtcctcctgt ttcatccaag | 1440 |
| cgtgtaaggg tccccgtcct tgactcccta gtgtcctgct gcccacagtc cagtcctggg | 1500 |
| aaccagcacc gatcacctcc catcgggcca atctcagtcc cttccccct acgtcggggc | 1560 |
| ccacacgctc ggtgcgtgcc cagttgaacc aggcggctgc ggaaaaaaaa aagcggggag | 1620 |
| aaagtagggc ccggctacta gcggttttac gggcgcacgt agctcaggcc tcaagaccttt | 1680 |
| gggctgggac tggctgagcc tggcgggagg cggggtccga gtcaccgcct gccgccgcgc | 1740 |
| ccccggtttc tataaattga gcccgcagcc tcccgcttcg ctctctgctc ctcctgttcg | 1800 |
| acagtcagcc gcatcttctt ttgcgtcgcc agcgtctcag gggccctggc agaactcggt | 1860 |
| aagtctgttg acatgtatgt gatgtatact aacctgcatg ggacgtggat ttacttgtgt | 1920 |

-continued

```
atgtcagata gagtaaagat taactcttgc atgtgagcgg ggcatcgaga tagcgataaa    1980
tgagtcagga ggacggatac ttatatgtgt tgttatcctc ctctacagtc aaacagatta    2040
aggggtagct tgcttgttct ttttgcagaa gctcagaata aacgctcaac tttggccgcc    2100
accatg                                                              2106
```